(12) United States Patent
Chi et al.

(10) Patent No.: US 9,120,721 B2
(45) Date of Patent: Sep. 1, 2015

(54) METHOD OF PREPARING CHIRAL KETONES FROM ALDEHYDES

(71) Applicant: Nanyang Technological University, Singapore (SG)

(72) Inventors: Yonggui Chi, Singapore (SG); Bhoopendra Tiwari, Singapore (SG)

(73) Assignee: Nanyang Technological University, Singapore (SG)

( * ) Notice: Subject to any disclaimer, the term of this patent is extended or adjusted under 35 U.S.C. 154(b) by 0 days.

(21) Appl. No.: 14/359,847

(22) PCT Filed: Dec. 13, 2012

(86) PCT No.: PCT/SG2012/000474
§ 371 (c)(1),
(2) Date: May 21, 2014

(87) PCT Pub. No.: WO2013/095301
PCT Pub. Date: Jun. 27, 2013

(65) Prior Publication Data
US 2014/0309459 A1    Oct. 16, 2014

Related U.S. Application Data

(60) Provisional application No. 61/577,508, filed on Dec. 19, 2011.

(51) Int. Cl.
*C07C 211/00*    (2006.01)
*C07C 205/00*    (2006.01)
(Continued)

(52) U.S. Cl.
CPC .............. *C07C 221/00* (2013.01); *C07B 41/06* (2013.01); *C07C 201/12* (2013.01); *C07C 205/02* (2013.01); *C07C 205/44* (2013.01); *C07C 225/14* (2013.01); *C07C 225/16* (2013.01)

(58) Field of Classification Search
None
See application file for complete search history.

(56) References Cited

PUBLICATIONS

Ando et al., "Singlet Oxygen Reaction. IV. Photooxygenation of Enamines Involving a Two-Step Cleavage of a 1,2-Dioxetane Intermediate," *Journal of the American Chemical Society* 97(17):5028-5029, 1975.

(Continued)

*Primary Examiner* — Clinton Brooks
(74) *Attorney, Agent, or Firm* — Seed IP Law Group PLLC

(57) ABSTRACT

Present invention relates to a method of preparing a chiral α- or β-substituted ketone from the corresponding β- or γ-substituted aldehyde, wherein the ketone has formula (I), (III) or (V), and the corresponding aldehyde has formula (II), (IV) or (VI), respectively, the method comprising reacting the aldehyde of formula (II), (IV) or (VI) in the presence of an amine, oxygen and an organic solvent, wherein the reaction is carried out in the absence of a metal-based catalyst or a metal-based oxidant, wherein: R is H, a substituted or unsubstituted $C_1$-$C_{10}$ alkyl, substituted or unsubstituted $C_2$-$C_{15}$ alkenyl, substituted or unsubstituted $C_2$-$C_{15}$ alkynyl, substituted or unsubstituted $C_3$-$C_{15}$ cycloalkyl, substituted or unsubstituted $C_3$-$C_{15}$ cycloalkenyl, substituted or unsubstituted $C_3$-$C_{15}$ heterocycloalkyl, substituted or unsubstituted $C_3$-$C_{15}$ heterocycloalkenyl, substituted or unsubstituted $C_6$-$C_{15}$ aryl, or substituted or unsubstituted $C_6$-$C_{15}$ heteroaryl; and R' is H, a substituted or unsubstituted $C_1$-$C_{10}$ alkyl, substituted or unsubstituted $C_2$-$C_{15}$ alkenyl, substituted or unsubstituted $C_2$-$C_{15}$ alkynyl, substituted or unsubstituted $C_3$-$C_{15}$ cycloalkyl, substituted or unsubstituted $C_3$-$C_{15}$ cycloalkenyl, substituted or unsubstituted $C_3$-$C_{15}$ heterocycloalkyl, substituted or unsubstituted $C_3$-$C_{15}$ heterocycloalkenyl, substituted or unsubstituted $C_6$-$C_{15}$ aryl, or substituted or unsubstituted $C_6$-$C_{15}$ heteroaryl.

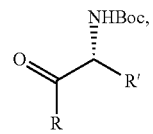

(I)

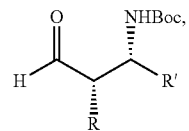

(II)

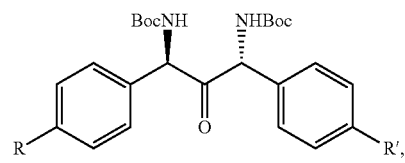

(III)

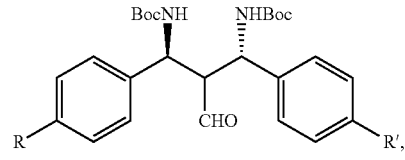

(IV)

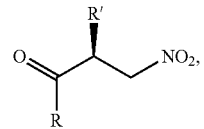

(V)

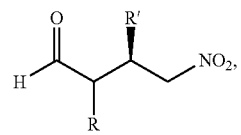

(VI)

18 Claims, No Drawings

(51) Int. Cl.
| | |
|---|---|
| C07C 207/00 | (2006.01) |
| C07C 221/00 | (2006.01) |
| C07C 201/12 | (2006.01) |
| C07C 205/02 | (2006.01) |
| C07C 205/44 | (2006.01) |
| C07B 41/06 | (2006.01) |
| C07C 225/14 | (2006.01) |
| C07C 225/16 | (2006.01) |

(56) References Cited

PUBLICATIONS

Barta et al., "Practical Modifications and Applications of the Sharpless Asymmetric Aminohydroxylation in the One-Pot Preparation of Chrial Oxazolidin-2-ones," *Organic Letters* 2(18):2821-2824, 2000.
Basran et al., "The Mechanism of Formation of N-Formylkynurenine by Heme Dioxygenases," *Journal of the American Chemical Society* 133:16251-16257, 2011.
Benhaliliba et al., "Solvent Free Oxidation of β, β-Disubstituted Enamines under Microwave Irradiation," *Tetrahedron Letters* 39:541-542, 1998.
Bernardi et al., "Concise and Sterocontrolled Synthesis of Pseudo-$C_2$-symmetric Diamino Alcohols and Triamines for Use in HIV Protease Inhibitors," *J. Org. Chem.* 68:1418-1425, 2003.
Bertelsen et al., "Organocatalysis—after the gold rush," *Chemical Society Reviews* 38:2178-2189, 2009.
Biju et al., "Extending NHC-Catalysis: Coupling Aldehydes with Unconventional Reaction Partners," *Accounts of Chemical Research* 44(11):1182-1195, 2011.
Bishop III, "Transition Metal Catalyzed Rearrangements of Small Ring Organic Molecules," *Chemical Reviews* 76(4):461-486, 1976.
Blau et al., "Studies on the Oxidation of Enamines with Molecular Oxygen 2. Oxidation of 1-Amino But-1-enes," *Journal f. prakt. Chemie.* 331(4):671-676, 1989.
Blau et al., "Studies on the Oxidation of Enamines with Molecular Oxygen. III Oxidation of Some Amino Styrenes," *Journal f. prakt. Chemie.* 333(3):455-466, 1991.
Cahiez et al., "Cobalt-Catalyzed Cross-Coupling Reactions," *Chem. Rev.* 110:1435-1462, 2010.
Chandler et al., "The Proline-Catalyzed Double Mannich Reaction of Acetaldehyde with N-Boc Imines," *Angew. Chem. Int. Ed.* 48:1978-1980, 2009.
Chiang et al., "N-Mesityl Substituted Chiral Triazolium Salts: Opening a New World of N-Heterocyclic Carbene Catalysis," *TCI Mail* 149:2-17, 2011.
Córdova et al., "The Direct Amino Acid-Catalyzed Asymmetric Incorporation of Molecular Oxygen to Organic Compounds," *J. Am. Chem. Soc.* 126:8914-8915, 2004.
Crabtree, "The Organometallic Chemistry of Alkanes," *Chem. Rev.* 85:245-269, 1985.
Crabtree, "Clipping the carbon-carbon bond," *Nature* 408:415-416, 2000.
DiRocco et al., "Catalytic Asymmetric Intermolecular Stetter Reaction of Heterocyclic Aldehydes with Nitroalkenes: Backbone Fluorination Improves Selectivity," *J. Am. Chem. Soc.* 131:10872-10874, 2009.
DiRocco et al., "Catalytic Asymmetric Intermolecular Stetter Reaction of Enals with Nitroalkenes: Enhancement of Catalytic Efficiency through Bifunctional Additives," *J. Am. Chem. Soc.* 133:10402-10405, 2011.
Draghici et al., "Lewis Acid Promoted Carbon-Carbon Bond Cleavage of γ-Silyloxy-β-hydroxy-α-diazoesters," *J. Am. Chem. Soc.* 130:3766-3767, 2008.
Enders et al., "Organocatalysis by N-Hterocyclic Carbenes," *Chem. Rev.* 107:5606-5655, 2007.
Enders et al., "Asymmetric Synthesis of β-Nitro Ketones via Michael Addition of Lithiated α-Amino Nitriles to Nitroalkenes," *J. Org. Chem.* 73:9641-9646, 2008.

Erickson et al., "Design, Activity, and 2.8 Å Crystal Structure of a $C_2$ Symmetric Inhibitor Complexed to HIV-1 Protease," *Science* 249:527-533, 1990.
Foote et al., "Chemistry of Singlet Oxygen. VI. Photooxygenation of Enamines: Evidence for an Intermediate," *Tetrahedron letters* 29:3267-3270, 1968.
Ghorai et al., "$BF_3 \cdot OEt_2$-Mediated Highly Regioselective $S_N2$-Type Ring-Opening of N-Activated Aziridines and N-Activated Azetidines by Tetraalkylammonium Halides," *J. Org. Chem.* 75:137-151, 2010.
Han et al., "Cleavage of Carbon-Carbon Bonds through the Mild Release of Trifluoroacetate: Generation of α,α-Difluoroenolates for Aldol Reactions," *J. Am. Chem. Soc.* 133:5802-5805, 2011.
Harris et al., "A Facile Dehomologation of α-Substituted Aldehydes to the Corresponding Ketones," *Tetrahedron Letters* 36(17):2921-2924, 1995.
Harris et al., "Enamine Oxidations. 2. Selective Oxidative Cleavage of β,β-Disubstituted Enamines Using Alumina Supported Permanganate. Synthesis of One-Carbon Dehomologated Carbonyl Compounds from Enamines," *Tetrahedron Letters* 38(6):981-984, 1997.
Hayashi et al., "Diphenylprolinol Silyl Ethers as Efficient Organocatalysts for the Asymmetric Michael Reaction of Aldehydes and Nitroalkenes," *Angew. Chem. Int. Ed.* 44:4212-4215, 2005.
Huber, "Photooxygenation of Enamines—A Partial Synthesis of Progesterone," *Tetrahedron Letters* 29:3271-3272, 1968.
Jennings et al., "Metallacyclobutane Complexes of the Group Eight Transition Metals: Synthesis, Characterizations, and Chemistry," *Chem. Rev.* 94:2241-2290, 1994.
Kamijo et al., "A Tandem Carbanion Addition/Carbon-Carbon Bond Cleavage Yields Alkynyl Ketones," *J. Am. Chem. Soc.* 127:5028-5029, 2005.
Kaneda et al., "Oxygenation of Enamines Using Copper Catalysts," *Journal of Molecular Catalysis* 15:349-365, 1982.
Kumaragurubaran et al., "Direct $_L$-Proline-Catalyzed Asymmetric α-Amination of Ketones," *J. Am. Chem. Soc.* 124:6254-6255, 2002.
Lee et al., "Catalytic Asymmetric Electrophilic α-Amination of α-Cyanoketones in the Presence of Chrial Palladium Complexes," *Synlett* 12:1821-1824, 2008.
Marion et al., "N-Heterocyclic Carbenes as Organocatalysts," *Angew. Chem. Int. Ed.* 46:2988-3000, 2007.
Mattson et al., "Direct Nucleophilic Acylation of Nitroalkenes Promoted by a Fluoride Anion/Thiourea Combination," *J. Am. Chem. Soc.* 128:4932-4933, 2006.
McDonald et al., "Palladium (II)-Catalyzed Alkene Functionalization via Nucleopalladation: Stereochemical Pathways and Enantioselective Catalytic Applications," *Chemical Reviews* 111:2981-3019, 2011.
Molnár, "Efficient, Selective, and Recyclable Palladium Catalysts in Carbon-Carbon Coupling Reactions," *Chemical Reviews* 111:2251-2320, 2011.
Muñiz et al., "2-Amino ketones from osmium-catalysed oxidations of alkenes," *Journal of Molecular Catalysis A: Chemical* 251:277-285, 2006.
Nair et al., "Recent advances in carbon-carbon bond-forming reactions involving homoenolates generated by NHC catalysis," *Chemical Society Reviews* 37:2691-2698, 2008.
Nicewicz et al., "Merging Photoredox Catalysis with Organocatalysis: The Direct Asymmetric Alkylation of Aldehydes," *Science* 322:77-80, 2008.
Nicolaou et al., "Palladiumkatalysierte Kreuzkupplungen in der Totalsynthese," *Angew. Chem.* 117:4516-4563, 2005.
Ono, *The Nitro Group in Organic Synthesis*, Wiley-VCH, New York, 2001, 383 pages.
Payette et al., "Nitrosobenzene-Mediated C-C Bond Cleavage Reactions and Spectral Observation of an Oxazetidin-4-one Ring System," *J. Am. Chem. Soc.* 130:12276-12278, 2008.
Phillips et al., "Discovering New Reactions with N-Heterocyclic Carbene Catalysis," *Aldrichimica Acta* 42(3):55-66, 2009.
Pohlhaus et al., "Lewis Acid-Promoted Carbon-Carbon Bond Cleavage of Aziridines: Divergent Cycloaddition Pathways of the Derived Ylides," *J. Am. Chem. Soc.* 126:2294-2295, 2004.

(56) References Cited

OTHER PUBLICATIONS

Rybtchinski et al., "Metallinsertion in C-C-Bindungen in Lösung," *Angew. Chem.* 111:918-932, 1999.

Slomp, Jr. et al., "A Synthesis of Pregnane-3,20-dione from Sigmasterol and Ergosterol," *Journal of the American Chemical Society* 77:1216-1221, 1955.

Sreekumar et al., "Zeolite Supported Permanganate: An Efficient Catalyst for Selective Oxidation of Enamines, Alkylarenes and Unsaturated Alcohols," *Tetrahedron Letters* 38(29):5143-5146, 1997.

Thomassigny et al., "Amino acid-catalyzed asymmetric α-amination of carbonyls," *Tetrahedron Letters* 47:1117-1119, 2006.

Tiwari et al., "Facile Access to Chiral Ketones through Metal-Free Oxidative C-C Bond Cleavage of Aldehydes by $O_2$," *Angew. Chem. Int. Ed.* 51:1911-1914, 2012.

Uehara et al., "Organocatalytic asymmetric assembly reactions for the synthesis of carbohydrate derivatives by intermolecular Michael-Henry reactions," *PNAS* 107(48):20672-20677, 2010.

Van Rheenen, "Copper-catalysed Oxygenation of Enamines," *Chemical Communications* 6:314-315, 1969.

Vetelino et al., "A Mild Method for the Conversion of Activated Aryl Methyl Groups to Carboxaldehydes Via the Uncatalyzed Periodate Cleavage of Enamines," *Tetrahedron Letters* 35(2):219-222, 1994.

Vora et al., "Asymmetric N-Heterocyclic Carbene (NHC) Catalyzed Acyl Anion Reactions," *Aldrichmica Acta* 44(1):3-11, 2011.

Witkop, "Imine-Enamine Systems and the Mechanism of their Oxidation," *Journal of the American Chemical Society* 78:2873-2882, 1956.

Yang et al., "Practical Proline-catalyzed asymmetric Mannich reaction of aldehydes with *N*-Boc-imines," *Nature Protocols* 2(8):1937-1942, 2007.

Zhang et al., "Copper-Catalyzed Aerobic Oxidative Coupling of Aryl Acetaldehydes with Anilines Leading to α-Ketoamides," *Angew. Chem. Int. Ed.* 50:11088-11092, 2011.

METHOD OF PREPARING CHIRAL KETONES FROM ALDEHYDES

CROSS-REFERENCE TO RELATED APPLICATION

This application claims the benefit of priority of U.S. Provisional Patent Application No. 61/577,508, filed 19 Dec. 2011, the contents of which being hereby incorporated by reference in its entirety for all purposes.

TECHNICAL FIELD

The invention relates to methods of preparing chiral ketones from aldehydes, and in particular, chiral α- or (β-substituted ketones from the corresponding β- or γ-substituted aldehydes. More specifically, the invention relates to methods of preparing chiral α-amino ketones, α,α'-diamino ketones and β-nitro ketones.

BACKGROUND

Functionalized chiral ketones, such as α-amino ketones, α,α'-diamino ketones, β-nitro ketones, and their derivatives, are prevalent building blocks and ubiquitous subunits present in natural products and pharmaceutical leads. The synthesis of chiral ketones can be achieved via direct α-substitutions. For example, the synthesis of α-amino ketones has been achieved via catalytic amination of ketones by diethyl diazenedicarboxylate (DEAD). Despite the success, some drawbacks of this method lie in the unsatisfactory and/or undesired regio-selectivities for unsymmetric ketones and to certain extent the demanding conditions required for subsequent N—N bond cleavages.

Recently, a metal-free nitrosobenzene mediated C—C bond cleavage for esters and 1,3-diketo compounds was developed. The C—C bond cleaving transformations for achiral aldehydes have been studied since the 1950s via oxidation of the corresponding preformed enamines in the presence of strong metal oxidants or catalysts. However, nearly all the reported reactions for C—C bond cleavage of aldehydes were sluggish with the formation of multiple side products (or even dominating undesired products) due to the non-selective conditions. Furthermore, these methods only deal with achiral and simple aldehydes bearing no useful functional groups.

Therefore, there remains a need to provide for methods to prepare functionalized chiral ketones in order to overcome, or at least alleviates, the above drawbacks.

SUMMARY

Disclosed herein is the C—C bond cleavage of chiral aldehydes by molecular oxygen ($O_2$) for the facile access to optically enriched or chiral ketones, such as α-amino ketones, α,α'-diamino ketones, and β-nitro ketones. Coupling the availability of the large number of enantioselective methods for the preparation of chiral aldehydes with the use of inexpensive amino catalysts, the present methods are thus applicable to the synthesis of a wide range of useful molecules. Present methods also stimulate new synthetic designs in building complex molecules.

Thus, in one aspect of the invention, there is provided a method of preparing a chiral α- or β-substituted ketone from the corresponding β- or γ-substituted aldehyde, wherein the ketone has formula (I), (III) or (V),

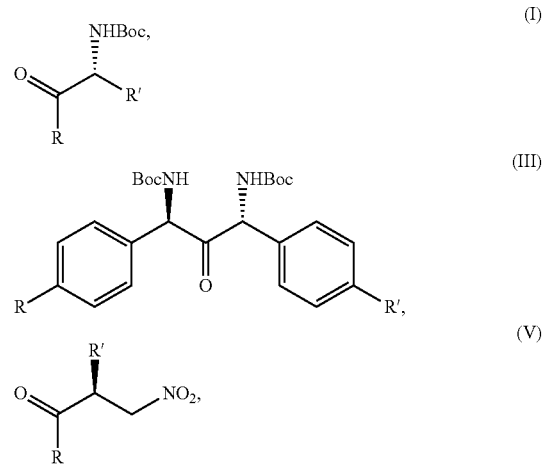

and the corresponding aldehyde has formula (II), (IV) or (VI), respectively,

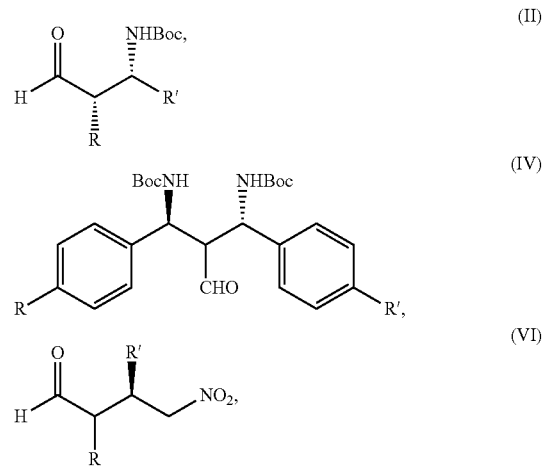

the method comprising reacting the aldehyde of formula (II), (IV) or (VI) in the presence of an amine, oxygen and an organic solvent, wherein the reaction is carried out in the absence of a metal-based catalyst or a metal-based oxidant, wherein:
R is H, a substituted or unsubstituted $C_1$-$C_{10}$ alkyl, substituted or unsubstituted $C_2$-$C_{15}$ alkenyl, substituted or unsubstituted $C_2$-$C_{15}$ alkynyl, substituted or unsubstituted $C_3$-$C_{15}$ cycloalkyl, substituted or unsubstituted $C_3$-$C_{15}$ cycloalkenyl, substituted or unsubstituted $C_3$-$C_{15}$ heterocycloalkyl, substituted or unsubstituted $C_3$-$C_{15}$ heterocycloalkenyl, substituted or unsubstituted $C_6$-$C_{15}$ aryl, or substituted or unsubstituted $C_6$-$C_{15}$ heteroaryl; and R' is H, a substituted or unsubstituted $C_1$-$C_{10}$ alkyl, substituted or unsubstituted $C_2$-$C_{15}$ alkenyl, substituted or unsubstituted $C_2$-$C_{15}$ alkynyl, substituted or unsubstituted $C_3$-$C_{15}$ cycloalkyl, substituted or unsubstituted $C_3$-$C_{15}$ cycloalkenyl, substituted or unsubstituted $C_3$-$C_{15}$ heterocycloalkyl, substituted or unsubstituted $C_3$-$C_{15}$ heterocycloalkenyl, substituted or unsubstituted $C_6$-$C_{15}$ aryl, or substituted or unsubstituted $C_6$-$C_{15}$ heteroaryl.

In one embodiment, the amine (i.e. amino catalyst) is

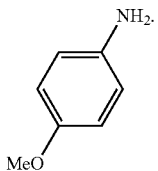

In another embodiment, the organic solvent is toluene.

The oxygen may be provided by carrying out the reaction in the presence of an oxygen-containing atmosphere, such as air.

DESCRIPTION

The following detailed description refers to the accompanying drawings that show, by way of illustration, specific details and embodiments in which the invention may be practised. These embodiments are described in sufficient detail to enable those skilled in the art to practise the invention. Other embodiments may be utilized and changes may be made without departing from the scope of the invention. The various embodiments are not necessarily mutually exclusive, as some embodiments can be combined with one or more other embodiments to form new embodiments.

Limitations or drawbacks associated with conventional new bond forming reactions for chiral ketone synthesis are substantially overcome or alleviated by the present C—C bond cleaving approach illustrated in Eq. (1),

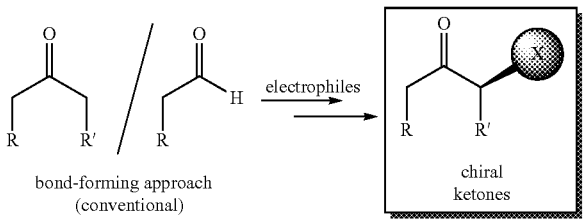

The moiety X in Eq. (1) may be an amino group —NHBoc where Boc represents di-tert-butyldicarbonate protecting group.

C—C bond cleavages hold tremendous potentials in synthesis but have remained under-developed in part due to the inherent inert nature of the C—C bonds. Existing studies have mainly restricted to the use of transition metal reagents or catalysts.

The present inventors have surprisingly found that the C—C bond cleavage of chiral aldehydes by molecular oxygen ($O_2$) provides for the facile access to optically enriched or chiral ketones, such as α-amino ketones, α,α'-diamino ketones, and β-nitro ketones. Coupling the availability of the large number of enantioselective methods for the preparation of chiral aldehydes with the use of inexpensive amino catalysts, the present methods are thus applicable to the synthesis of a wide range of useful molecules. Present methods also stimulate new synthetic designs in building complex molecules. Advantageously, the present methods do not involve the use of metal-based catalysts or metal-based oxidants or reagents, thereby avoiding the drawbacks of existing methods involving the use of transition metal reagents or catalysts.

Thus, one aspect of the invention provides for a method of preparing a chiral α- or β-substituted ketone from the corresponding β- or γ-substituted aldehyde, wherein the ketone has formula (I), (III) or (V),

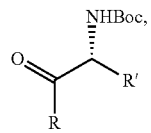
(I)

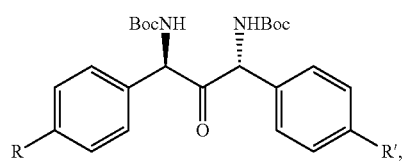
(III)

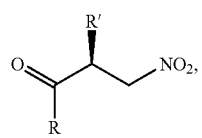
(V)

and the corresponding aldehyde has formula (II), (IV) or (VI), respectively,

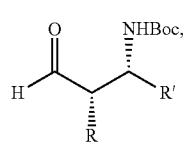
(II)

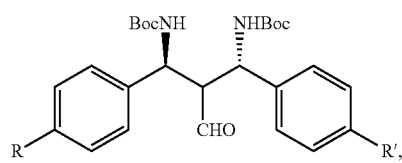
(IV)

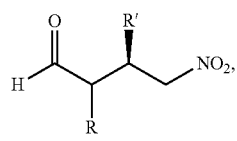
(VI)

the method comprising reacting the aldehyde in the presence of an amine, oxygen and an organic solvent, wherein the reaction is carried out in the absence of a metal-based catalyst or a metal-based oxidant.

The oxygen may be provided by carrying out the reaction in the presence of an oxygen-containing atmosphere, such as air.

R may be H, a substituted or unsubstituted $C_1$-$C_{10}$ alkyl, substituted or unsubstituted $C_2$-$C_{15}$ alkenyl, substituted or unsubstituted $C_2$-$C_{15}$ alkynyl, substituted or unsubstituted $C_3$-$C_{15}$ cycloalkyl, substituted or unsubstituted $C_3$-$C_{15}$ cycloalkenyl, substituted or unsubstituted $C_3$-$C_{15}$ heterocycloalkyl, substituted or unsubstituted $C_3$-$C_{15}$ heterocycloalkenyl, substituted or unsubstituted $C_6$-$C_{15}$ aryl, or substituted or unsubstituted $C_6$-$C_{15}$ heteroaryl.

R' may be H, a substituted or unsubstituted $C_1$-$C_{10}$ alkyl, substituted or unsubstituted $C_2$-$C_{15}$ alkenyl, substituted or unsubstituted $C_2$-$C_{15}$ alkynyl, substituted or unsubstituted $C_3$-$C_{15}$ cycloalkyl, substituted or unsubstituted $C_3$-$C_{15}$ cycloalkenyl, substituted or unsubstituted $C_3$-$C_{15}$ heterocycloalkyl, substituted or unsubstituted $C_3$-$C_{15}$ heterocycloalkenyl, substituted or unsubstituted $C_6$-$C_{15}$ aryl, or substituted or unsubstituted $C_6$-$C_{15}$ heteroaryl.

The term "aliphatic", alone or in combination, refers to a straight chain or branched chain hydrocarbon comprising at least one carbon atom. Aliphatics include alkyls, alkenyls, and alkynyls. In certain embodiments, aliphatics are optionally substituted, i.e. substituted or unsubstituted. Aliphatics include, but are not limited to, methyl, ethyl, propyl, isopropyl, butyl, isobutyl, tert-butyl, pentyl, hexyl, ethenyl, propenyl, butenyl, ethynyl, butynyl, propynyl, and the like, each of which may be optionally substituted. As used herein, aliphatic is not intended to include cyclic groups.

The term "optionally substituted" or "substituted or unsubstituted" refers to a group in which none, one, or more than one of the hydrogen atoms have been replaced with one or more groups such as, but are not limited to, alkyl, alkenyl, alkynyl, heteroalkyl, cycloalkyl, aryl, alkylaryl, or heteroaryl.

The term "alkyl", alone or in combination, refers to a fully saturated aliphatic hydrocarbon. In certain embodiments, alkyls are optionally substituted, i.e. substituted or unsubstituted. In certain embodiments, an alkyl comprises 1 to 10 carbon atoms, for example 2 to 8 carbon atoms, wherein (whenever it appears herein in any of the definitions given below) a numerical range, such as "1 to 10" or "$C_1$-$C_{10}$", refers to each integer in the given range, e.g. "$C_1$-$C_{10}$ alkyl" means that an alkyl group comprising only 1 carbon atom, 2 carbon atoms, 3 carbon atoms, 4 carbon atoms, 5 carbon atoms, 6 carbon atoms, 7 carbon atoms, 8 carbon atoms, 9 carbon atoms, or 10 carbon atoms. Examples of alkyl groups include, but are not limited to, methyl, ethyl, n-propyl, isopropyl, n-butyl, isobutyl, sec-butyl, tert-butyl, tert-amyl, pentyl, hexyl, heptyl, octyl and the like. In certain embodiments, one or more carbon atoms may be replaced by a heteroatom to form a heteroalkyl (see definition below).

The term "alkenyl", alone or in combination, refers to an aliphatic hydrocarbon having one or more carbon-carbon double-bonds, such as two or three carbon-carbon double-bonds. In certain embodiments, alkenyls are optionally substituted, i.e. substituted or unsubstituted. In certain embodiments, an alkenyl comprises 2 to 15 carbon atoms, for example 2 to 10 carbon atoms. "$C_2$-$C_{15}$ alkenyl" means that an alkenyl group comprising only 2 carbon atoms, 3 carbon atoms, 4 carbon atoms, 5 carbon atoms, 6 carbon atoms, 7 carbon atoms, 8 carbon atoms, 9 carbon atoms, 10 carbon atoms, 11 carbon atoms, 12 carbon atoms, 13 carbon atoms, 14 carbon atoms, or 15 carbon atoms. Examples of alkenyls include, but are not limited to, ethenyl, propenyl, butenyl, 1,4-butadienyl, pentenyl, hexenyl, 4-methylhex-1-enyl, 4-ethyl-2-methylhex-1-enyl and the like. In certain embodiments, one or more carbon atoms may be replaced by a heteroatom to form a heteroalkenyl (see definition below).

The term "alkynyl", alone or in combination, refers to an aliphatic hydrocarbon having one or more carbon-carbon triple-bonds, such as two or three carbon-carbon triple-bonds. In certain embodiments, alkynyls are optionally substituted, i.e. substituted or unsubstituted. In certain embodiments, an alkynyl comprises 2 to 15 carbon atoms, for example 2 to 10 carbon atoms. "$C_2$-$C_{15}$ alkynyl" means that an alkynyl group comprising only 2 carbon atoms, 3 carbon atoms, 4 carbon atoms, 5 carbon atoms, 6 carbon atoms, 7 carbon atoms, 8 carbon atoms, 9 carbon atoms, 10 carbon atoms, 11 carbon atoms, 12 carbon atoms, 13 carbon atoms, 14 carbon atoms, or 15 carbon atoms. Examples of alkynyls include, but are not limited to, ethynyl, propynyl, butynyl, and the like. In certain embodiments, one or more carbon atoms may be replaced by a heteroatom to form a heteroalkynyl (see definition below).

The term "aromatic" refers to a group comprising a covalently closed planar ring having a delocalized [pi]-electron system comprising 4n+2 [pi] electrons, where n is an integer. Aromatic rings may be formed by five, six, seven, eight, nine, or more than nine atoms. Aromatics may be optionally substituted. Examples of aromatic groups include, but are not limited to phenyl, naphthalenyl, phenanthrenyl, anthracenyl, tetralinyl, fluorenyl, indenyl, and indanyl. The term aromatic includes, for example, benzenoid groups, connected via one of the ring-forming carbon atoms, and optionally carrying one or more substituents selected from an aryl, a heteroaryl, a cycloalkyl, a non-aromatic heterocycle, a halo, a hydroxy, an amino, a cyano, a nitro, an alkylamido, an acyl, a $C_1$-$C_6$ alkoxy, a $C_1$-$C_6$ alkyl, a $C_1$-$C_6$ hydroxyalkyl, a $C_1$-$C_6$ aminoalkyl, an alkylsulfenyl, an alkylsulfinyl, an alkylsulfonyl, an sulfamoyl, or a trifluoromethyl. In certain embodiments, an aromatic group is substituted at one or more of the para, meta, and/or ortho positions. Examples of aromatic groups comprising substitutions include, but are not limited to, phenyl, 3-halophenyl, 4-halophenyl, 3-hydroxyphenyl, 4-hydroxyphenyl, 3-aminophenyl, 4-aminophenyl, 3-methylphenyl, 4-methylphenyl, 3-methoxyphenyl, 4-methoxyphenyl, 4-trifluoromethoxyphenyl, 3-cyanophenyl, 4-cyanophenyl, dimethylphenyl, naphthyl, hydroxynaphthyl, hydroxymethylphenyl, (trifluoromethyl)phenyl, alkoxyphenyl, 4-morpholin-4-ylphenyl, 4-pyrrolidin-1-ylphenyl, 4-pyrazolylphenyl, 4-triazolylphenyl, and 4-(2-oxopyrrolidin-1-yl)phenyl.

The term "aryl" refers to an aromatic ring wherein each of the atoms forming the ring is a carbon atom. Aryl rings may be formed by five, six, seven, eight, nine, or more than nine carbon atoms. Aryl groups may be optionally substituted.

The term "heteroaryl" refers to an aromatic heterocycle. Heteroaryl rings may be formed by three, four, five, six, seven, eight, nine, or more than nine atoms. Heteroaryls may be optionally substituted. Examples of heteroaryl groups include, but are not limited to, aromatic $C_3$-$C_8$ heterocyclic groups comprising one oxygen or sulfur atom or up to four nitrogen atoms, or a combination of one oxygen or sulfur atom and up to two nitrogen atoms, and their substituted as well as benzo- and pyrido-fused derivatives, for example, connected via one of the ring-forming carbon atoms. In certain embodiments, heteroaryl groups are optionally substituted with one or more substituents, independently selected from halo, hydroxy, amino, cyano, nitro, alkylamido, acyl, $C_1$-$C_6$ alkoxy, $C_1$-$C_6$ alkyl, $C_1$-$C_6$ hydroxyalkyl, $C_1$-$C_6$ aminoalkyl, alkylsulfenyl, alkylsulfinyl, alkylsulfonyl, sulfamoyl, or trifluoromethyl. Examples of heteroaryl groups include, but are not limited to, unsubstituted and mono- or di-substituted derivatives of furan, benzofuran, thiophene, benzothiophene, pyrrole, pyridine, indole, oxazole, benzoxazole, isoxazole, benzisoxazole, thiazole, benzothiazole, isothiazole, imidazole, benzimidazole, pyrazole, indazole, tetrazole, quinoline, isoquinoline, pyridazine, pyrimidine, purine and pyrazine, furazan, 1,2,3-oxadiazole, 1,2,3-thiadiazole, 1,2,4-thiadiazole, triazole, benzotriazole, pteridine, phenoxazole, oxadiazole, benzopyrazole, quinolizine, cinnoline, phthalazine, quinazoline, and quinoxaline. In some embodiments, the substituents are halo, hydroxy, cyano, or $C_1$-$C_6$ alkyl.

The term "non-aromatic ring" refers to a group comprising a covalently closed ring that is not aromatic.

The term "alicyclic" refers to a group comprising a non-aromatic ring wherein each of the atoms forming the ring is a carbon atom. Alicyclic groups may be formed by three, four, five, six, seven, eight, nine, or more than nine carbon atoms. In certain embodiments, alicyclics are optionally substituted, i.e. substituted or unsubstituted. In certain embodiments, an alicyclic comprises one or more unsaturated bonds, such as one, two or three carbon-carbon double-bonds. Alicyclics include cycloalkyls and cycloalkenyls. Examples of cycloalkyls include, but are not limited to, cyclopropane, cyclobutane, cyclopentane, cyclohexane, and cycloheptane. Examples of cycloalkenyls include, but are not limited to, cyclopentene, cyclopentadiene, cyclohexene, 1,3-cyclohexadiene, 1,4-cyclohexadiene, and cycloheptene.

The term "heteroatom" refers to an atom other than carbon or hydrogen. Heteroatoms are typically independently selected from oxygen, sulfur, nitrogen, and phosphorus, but are not limited to those atoms. In embodiments in which two or more heteroatoms are present, the two or more heteroatoms may all be the same as one another, or some or all of the two or more heteroatoms may each be different from the others.

The term "heteroaliphatic", alone or in combination, refers to a group comprising an aliphatic hydrocarbon (such as alkyl, alkenyl, and alkynyl) and one or more heteroatoms. In certain embodiments, heteroaliphatics are optionally substituted, i.e. substituted or unsubstituted. Certain heteroaliphatics are acylaliphatics, in which the one or more heteroatoms are not within an aliphatic chain. Heteroaliphatics include heteroalkyls, including, but not limited to, acylalkyls, heteroalkenyls, including, but not limited to, acylalkenyls, and heteroalkynyls, including, but not limited acylalkynyls. Examples of heteraliphatics include, but are not limited to, $CH_3C(=O)CH_2-$, $CH_3C(=O)CH_2CH_2-$, $CH_3CH_2C(=O)CH_2CH_2-$, $CH_3C(=O)CH_2CH_2CH_2-$, $CH_3OCH_2CH_2-$, $CH_3NHCH_2-$, and the like.

The term "heterocycle" refers to a group comprising a covalently closed ring wherein at least one atom forming the ring is a carbon atom and at least one atom forming the ring is a heteroatom. Heterocyclic rings may be formed by three, four, five, six, seven, eight, nine, or more than nine atoms. Any number of those atoms may be heteroatoms (i.e., a heterocyclic ring may comprise one, two, three, four, five, six, seven, eight, nine, or more than nine heteroatoms). Herein, whenever the number of carbon atoms in a heterocycle is indicated (e.g., $C_1$-$C_6$ heterocycle), at least one other atom (the heteroatom) must be present in the ring. Designations such as "$C_1$-$C_6$ heterocycle" refer only to the number of carbon atoms in the ring and do not refer to the total number of atoms in the ring. It is understood that the heterocylic ring will have additional heteroatoms in the ring. In heterocycles comprising two or more heteroatoms, those two or more heteroatoms may be the same or different from one another. Heterocycles may be optionally substituted. Binding to a heterocycle can be at a heteroatom or via a carbon atom.

Examples of heterocycles include heterocycloalkyls (where the ring contains fully saturated bonds) and heterocycloalkenyls (where the ring contains one or more unsaturated bonds) such as, but are not limited to the following:

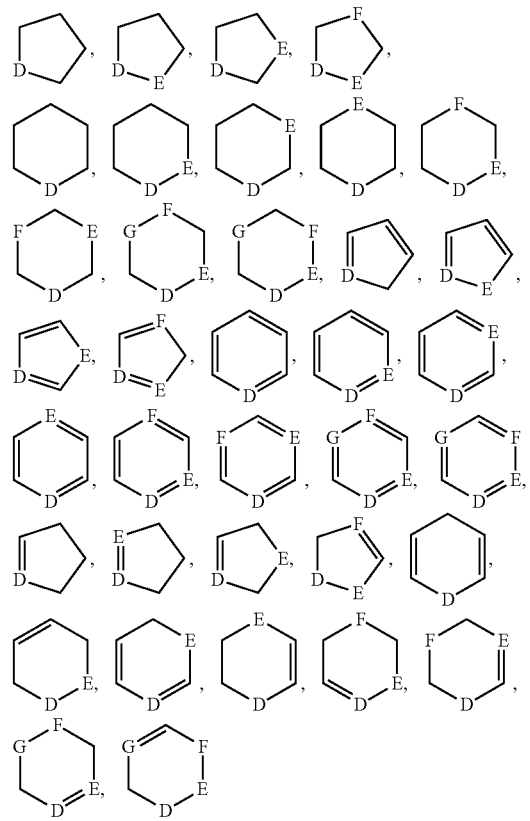

wherein D, E, F, and G independently represent a heteroatom. Each of D, E, F, and G may be the same or different from one another.

The term "ring" refers to any covalently closed structure. Rings include, for example, carbocycles (e.g., aryls and alicyclics), heterocycles (e.g., heteroaryls and non-aromatic heterocycles), aromatics (e.g., aryls and heteroaryls), and non-aromatics (e.g., alicyclics and non-aromatic heterocycles). Rings may be optionally substituted.

The term "alkylaryl" refers to a group comprising an aryl group bound to an alkyl group.

Without wishing to be bound by any theory, it is hypothesized that Eq. (1) proceeded via the following reaction mechanism: the C—C bond cleaving reaction is postulated to proceed through the decomposition of a dioxetane intermediate (iv), see Scheme 1 below. Detection of intermediate (iv) and its precursor (iii) via NMR ($^1$H and $^{13}$C NMR) and mass spectrometry was not successful. One evidence indicating the presence of the hydroperoxide intermediate (iii) was obtained via the starch-iodide test. While the exact reaction mechanism remains unclear, the decomposition of the dioxetane intermediate (iv) might follow a concerted pathway. If such type of dioxetane decomposition is concerted with some C—C and O—O bond rupture developing at the transition state, substituent (R) effects would be significant and vice-versa. It is observed that changing the R substituents of the Mannich adducts (see Example 3, Table 2, entries 1-4) had a significant effect on reaction time.

Scheme 1: Proposed reaction mechanism.

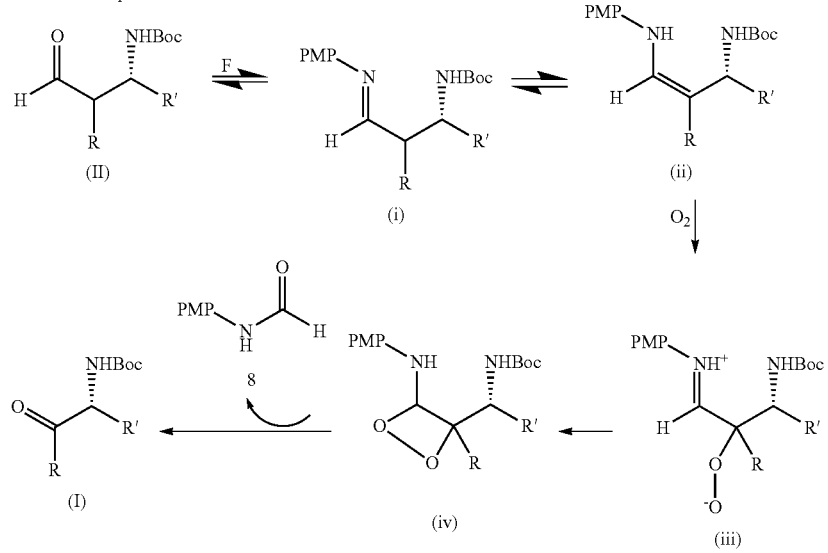

Various catalyst systems and reaction conditions for performing the oxidative C—C bond cleavage illustrated in Eq. (1) have been explored by the present inventors. A model reaction shown in Table 1, Example 2 below has been adopted and the process parameters optimized accordingly as elaborated in Example 2.

In various embodiments, the amine is a compound of formula (VII), $$R_1—NHR_2 \quad (VII),$$

wherein:
- $R_1$ is a substituted or unsubstituted alkylaryl, substituted or unsubstituted aryl, substituted or unsubstituted heteroaryl, substituted or unsubstituted alicyclic, substituted or unsubstituted heteroalicyclic, substituted or unsubstituted alkylcycloalkyl, substituted or unsubstituted alkylheterocycloalkyl; and
- $R_2$ is H or combines with $R_1$ to form with the nitrogen to which they are attached a cyclic group selected from substituted or unsubstituted heterocycloalkyl and substituted or unsubstituted heteroaryl.

In certain embodiments, the amine of formula (VII) is selected from the group consisting of

A

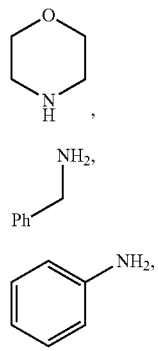

B

C

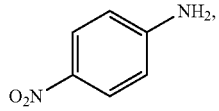

D

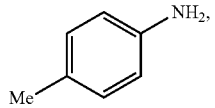

E

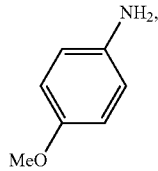

F

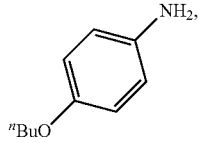

G and mixtures thereof.

In one embodiment, the amine of formula (VII) is

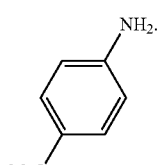

F

In various embodiments, the organic solvent is toluene, $CH_2CN$ or $CH_3Cl$. For example, the organic solvent may be toluene.

The aldehyde of formula (II), (IV) or (VI) may be reacted by heating the aldehyde at a temperature range of between 40 and 80° C., such as about 40° C., about 45° C., about 50° C., about 55° C., about 60° C., about 65° C., about 70° C., about 75° C., or about 80° C.

In various embodiments, the aldehyde of formula (II), (IV) or (VI) is reacted by heating at 50° C.

In certain embodiments, the aldehyde of formula (II), (IV) or (VI) is reacted by heating at 50° C. in the presence of toluene.

In various embodiments, heating of the aldehyde of formula (II), (IV) or (VI) is carried out for a period of between 1 and 48 h, such as between 1 and 36 h, between 1 and 24 h, or between 4 and 24 h. For example, heating of the aldehyde of formula (II), (IV) or (VI) may be carried out for 1 h, 2 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h, or 24 h.

In certain embodiments, the aldehyde of formula (II), (IV) or (VI) is reacted by heating at 50° C. in the presence of toluene for 4 to 24 h, such as 4 h.

In various embodiments, the reaction is carried out at a pressure of between 1 and 15 atm, such as 1 atm, 2 atm, 3 atm, 4 atm, 5 atm, 6 atm, 7 atm, 8 atm, 9 atm, 10 atm, 11 atm, 12 atm, 13 atm, 14 atm, or 15 atm. In one embodiment, the reaction is carried out at 10 atm.

In certain embodiments, the aldehyde of formula (II), (IV) or (VI) is reacted by heating at 50° C. in the presence of toluene for 4 to 24 h, such as 4 h, at 10 atm.

In yet certain embodiments, the ketone has formula (I) and the corresponding aldehyde has formula (III). In such embodiments, R may be selected from the group consisting of methyl, i-propyl, n-butyl, benzyl and 7-octenyl. In such further embodiments, R' may be selected from the group consisting of phenyl, 4-OMe-$C_6H_4$, 4-Cl—$C_6H_4$, 4-F—$C_6H_4$, 4-Br—$C_6H_4$, 2-Me-$C_6H_4$, 3-Me-$C_6H_4$, 4-Me-$C_6H_4$, and 2-Naph.

In other embodiments, the ketone has formula (III) and the corresponding aldehyde has formula (IV). In such embodiments, each of R and R' may be independently selected from the group consisting of H, F, methyl and methoxy.

In yet further other embodiments, the ketone has formula (V) and the corresponding aldehyde has formula (VI). In such embodiments, R may be selected from the group consisting of methyl, i-propyl, n-propyl, and n-butyl. In such further embodiments, R' may be selected from the group consisting of phenyl, 4-OMe-$C_6H_4$, 4-Cl—$C_6H_4$, 4-F—$C_6H_4$, 4-Br—$C_6H_4$, $C_6H_{11}$, i-propyl, and n-butyl.

In sum, the present inventors have developed a metal-free approach for the synthesis of chiral ketones using molecular $O_2$ as the sole oxidant for the C—C bond cleavage of chiral aldehydes via enamine intermediates formed in situ. Using present methods, α-amino ketones, β-nitro ketones and α,α'-diamino ketones, which are building blocks and subunits in natural products and pharmaceutical leads, can be prepared with high optical purities from readily available substrates. Moreover, α-amino ketones contain functional groups amenable to further transformations into useful molecules such as hydroxy amines and further to chiral oxazolidinone (used as a chiral auxiliary) and aziridines (see Scheme 2).

Scheme 2: Synthesis of oxazolidinone and aziridine.

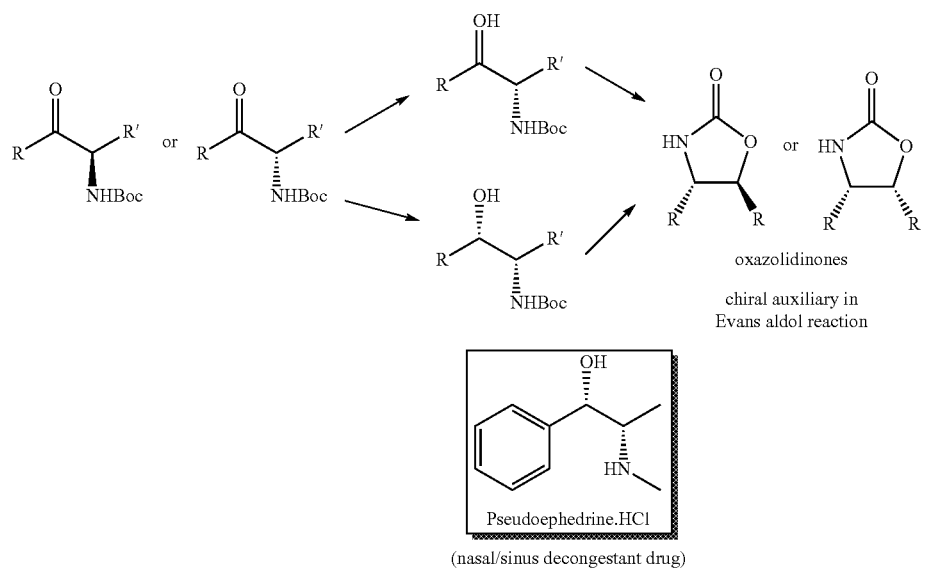

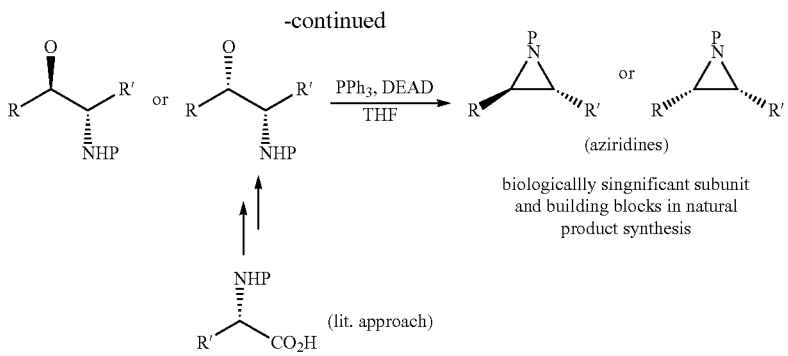

(A non asymmetric approach)
(Analogs from un-natural amino acid will be very expensive; where as our approach is silmiarly viable for both forms)

As demonstrated in Examples 19 and 24, α,α'-diamino ketone products can be easily transferred to optically pure diamino alcohols, where analogues of such diamino alcohols are key fragments in HIV-1 protease inhibitors (see Scheme 3).

Scheme 3: Diamino ketones to diamino alcohol (key-subunit of HIV-1protease inhibitor).

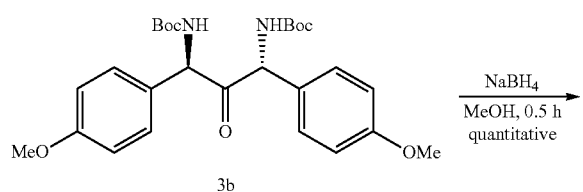

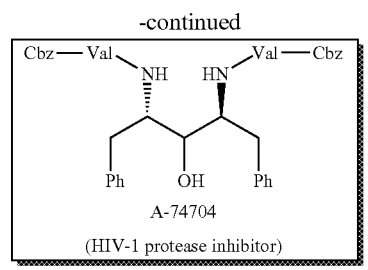

(HIV-1 protease inhibitor)

β-nitro ketones also contain functional groups amenable to further transformations into useful molecules such as β-amino ketones and 1,3-amino alcohols (useful as chiral ligand in asymmetric synthesis) and many other functionalities (see Scheme 4).

Scheme 4.

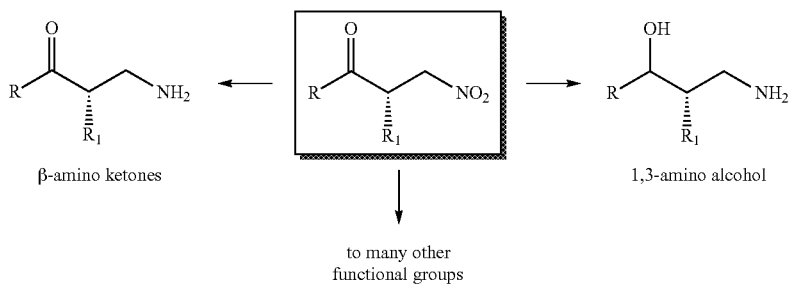

to many other functional groups

-continued

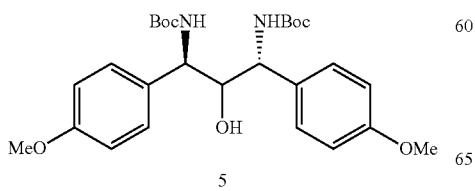

In order that the invention may be readily understood and put into practical effect, particular embodiments will now be described by way of the following non-limiting examples.

EXAMPLES

Example 1

General Methods and Materials

Commercially available materials purchased from Alfa Aesar or Aldrich was used as received, except aldehydes that were purified via distillation or column chromatography prior use. Proton nuclear magnetic resonance ($^1$H NMR) spectra were recorded on a JEOL ECA400 (400 MHz) or Bruker AV400 (400 MHz) spectrometers. Chemical shifts were recorded in parts per million (ppm, δ) relative to tetramethylsilane (δ0.00) or chloroform (δ=7.26, singlet). $^1$H NMR splitting patterns are designated as singlet (s), doublet (d), triplet (t), quartet (q), dd (doublet of doublets); m (multiplets), and etc. All first-order splitting patterns were assigned on the basis of the appearance of the multiplet. Splitting patterns that could not be easily interpreted are designated as multiplet (m) or broad (br). Carbon nuclear magnetic resonance ($^{13}$C NMR) spectra were recorded on a JEOL ECA400 (400 MHz) (100 MHz) or Bruker AV400 (400 MHz) (100 MHz) spectrometers. High resolution mass spectral analysis (HRMS) was performed on Finnigan MAT 95 XP mass spectrometer (Thermo Electron Corporation). The determination of ee was performed via chiral phase HPLC analysis using Shimadzu LC-20AD HPLC workstation. Optical rotations were measured using a 0.5 mL cell with a 10 mm path length on a PerkinElmer Model 341 digital polarimeter and are reported as follows: $[\alpha]_D^{rt}$ (c in g per mL solvent). Analytical thin-layer chromatography (TLC) was carried out on Merck 60 F254 pre-coated silica gel plate (0.2 mm thickness). Visualization was performed using a UV lamp or Ninhydrine stain. High pressure reactions were carried out in Paar-high pressure reactors (125 ml). A special precaution was taken in using toluene/O$_2$ especially at elevated temperatures.

Example 2

Model Reaction Optimization

Mannich adduct 2a was first used as a model substrate to develop an oxidative cleavage approach to furnish α-amino ketone 1a as the designed product (Table 1). The Mannich adduct substrates were prepared in essentially pure form without column chromatography starting from readily available materials (aldehydes and aryl imines) and inexpensive proline catalyst using List's protocol. Enamine intermediates are formed in situ for operational simplicity and to avoid complications in preparing pre-formed enamines of these chiral aldehydes containing functional groups. An initial survey of cyclic secondary amines (such as pyrrolidene, piperidine and morpholine) known in the literature for enamine oxidation did not lead to detectable amount of ketone product 1a using metal-based oxidants or metal catalysts under a range of conditions (Table 1, entries 1-4). Additional studies revealed that the use of primary amines in the presence of O$_2$ at 50° C. could afford the ketone product 1a with 12-34% isolated yield, and electron-rich phenyl amines performed better than alkyl amines (Table 1, entries 5-10). Inexpensive p-methoxy aniline (F) was thus chosed for further optimizations. With the presence of one equivalent of aniline F under ten atmosphere of O$_2$ at 50° C. in toluene, the ketone product 1a could be obtained in 91% yield and 99% ee (Table 1, entry 12). It was very fortunate to see no apparent erosion on the chiral center of the ketone product 1a. Increasing the loading of the amine reagent beyond 100 mol % did not show additional improvements (Table 1, entry 13). Brief solvents screening (Table 1, entries 14-15) indicated toluene as the solvent of choice.

TABLE 1

Model reaction optimization.

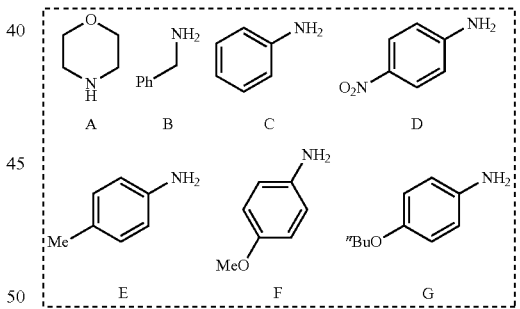

| entry[a] | conditions | yield [%][b] | ee [%][c] |
|---|---|---|---|
| 1[d] | A, CuCl, 1 atm O$_2$, CH$_3$CN, 70° C. | 0[e] | — |
| 2[d] | A, CuI, 1 atm O$_2$, CH$_3$CN, 70° C. | 0[e] | — |
| 3[d] | A, CuCl$_2$, 1 atm O$_2$, CH$_3$CN, 70° C. | 0[e] | — |
| 4[d] | A, CuCl$_2$, 1 atm O$_2$, toluene, 70° C. | 0[e] | — |
| 5 | B, 1 atm O$_2$, toluene, 50° C. | 12 | n.d. |
| 6 | C, 1 atm O$_2$, toluene, 50° C. | 15 | n.d. |
| 7 | D, 1 atm O$_2$, toluene, 50° C. | 0[e] | — |
| 8 | E, 1 atm O$_2$, toluene: 50° C. | 23 | n.d. |
| 9 | F, 1 atm O$_2$, toluene, 50° C. | 32 | n.d. |
| 10 | G, 1 atm O$_2$, toluene, 50° C. | 34 | n.d. |
| 11 | F, 10 atm O$_2$, toluene, rt | 0[e] | — |
| 12 | F, 10 atm O$_2$, toluene, 50° C. | 91 | 99 |
| 13[f] | F, 10 atm O$_2$, toluene, 50° C. | 88 | 97 |
| 14 | F, 10 atm O$_2$, CH$_3$CN, 50° C. | 43 | n.d. |
| 15 | F, 10 atm O$_2$, CH$_3$Cl, 50° C. | 12 | n.d. |

[a]Aldehyde 2a (0.15 mmol; 99% ee, >20:1 dr) and amine (0.15 mmol) in 1.5 mL solvent for 24 h.
[b]Isolated yield.
[c]Determined via chiral-phase HPLC analysis.
[d]20 mol % of metal catalyst.
[e]Via TLC and crude $^1$H NMR analysis.
[f]2.0 eq. of amine was used.

Example 3

Synthesis of α-Amino Ketones

To a Parr's high pressure reactor equipped with a magnetic stir bar were added aldehyde 2a (0.050 g, 0.15 mmol), p-methoxy aniline (0.018 g, 0.15 mmol) and toluene (1.5 mL). The reactor was then filled with O$_2$ to a reach a pressure of 10 atmospheres. The reaction mixture was stirred at room temperature for 1 h (presumably for imine/enamine formation), and then at 50° C. for 24 hours (for other substrates, the exact reaction temperature and time are indicated in Table 2). After complete consumption of aldehyde, as indicated by TLC (and crude $^1$H NMR analysis when necessary), the reaction mixture was concentrated in vacuo. Column chromatography (hexanes: EtOAc) of the resulting residue gave the desired α-amino ketone 1a (0.043 g, 0.013 mmol) as a yellowish oil in 91% yield.

The scope of amino aldehydes (2) with various R and R' substituents (Table 2) was examined. When R is a methyl (Table 2, entry 1) or n-alkyl group (Table 2, entry 2) and R' as a phenyl group, the reactions completed in 1-4 hours at room temperature to give the corresponding ketone products with excellent yields and optical purities. With other variations on the R substituents, such as alkenyl, branched alkyl or aryl or benzyl groups, longer reaction time (14-36 hours) and higher temperature (50° C.) were necessary (Table 2, entries 3-5). The effects of the electronic nature of the substituent on the aryl/R' group were then studied (Table 2, entries 6-11). The reactions proceeded to completion in 24-48 hours, giving products with excellent yields and optical purities with both electron donating (Table 2, entries 6-7, 12-14) and electron withdrawing substituents (Table 2, entries 8-11) on the R' groups. The substituent patterns on the R' aryls (ortho-, meta- and para-) showed no observed effects on the reaction outcomes (Table 2, entries 12-14).

To further demonstrate the simplicity of present method, List's catalytic Mannich reaction (J. W. Yang, M Stadler, B. List, *Nature Protocols*, 2007, 2, 1937-1942) and our oxidative cleavage were combined in a "single-pot" operation in a gram scale synthesis (eq 2). The crude Mannich reaction mixture was directly concentrated and subjected to the standard oxidative cleavage condition (Table 1, entry 12) to afford the corresponding ketone product 1a with 76% overall yield and 87% ee. The lower 87% ee was caused by the remained proline catalyst introduced during the Mannich reaction step. Thus a simple aqueous work-up (w/o chromatography purification of the Mannich adduct 2a) before the oxidative cleavage step could solve this problem. The ketone product was then obtained with 72% overall yield and 96% ee. It is of note that purification of the Mannich adduct 2a by filtration following the above literature procedure led to some product loss. A direct extraction here worked the best.

Example 4

(R)-tert-Butyl 1-(4-methoxyphenyl)-2-oxohexylcarbamate (1a)

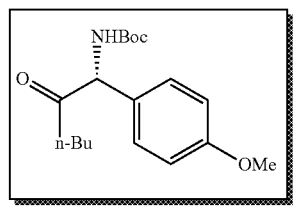

1a

The title compound was prepared according to the general procedure: Yellow oil, 91% yield; $[\alpha]_D^{20}$=-224.5° (c=0.015 g/mL, CHCl$_3$); $^1$H NMR (400 MHz, CDCl$_3$) δ 7.19 (d, J=8.3 Hz, 2H), 6.85 (d, J=8.4 Hz, 2H), 5.85 (d, J=5.5 Hz, 1H), 5.20 (d, J=6.3 Hz, 1H), 3.78 (s, 3H), 2.38-2.27 (m, 2H), 1.55-1.25 (m, 11H), 1.22-1.08 (m, 2H), 0.78 (t, J=7.3 Hz, 3H); $^{13}$C NMR (100 MHz, CDCl$_3$) δ 206.3, 159.5, 154.8, 129.0, 114.4, 79.6, 63.3, 55.2, 39.2, 28.2, 28.1, 25.7, 22.0, 13.6; HRMS (ESI) calcd for C$_{20}$H$_{26}$NO$_4$ (M+1)+: 344.1862. Found: 344.1859; HPLC analysis: 99% ee (Chiralcel AD-H, 02:98 $^i$PrOH/Hexane, 0.50 mL/min), R$_t$ (minor)=37.8 min, R$_t$ (major)=52.1 min.

TABLE 2

Synthesis of α-amino ketones.[a]

| entry | R | R' | 1 | time [h] | yield [%][b] | ee [%][c] |
|---|---|---|---|---|---|---|
| 1[d] | Me | Ph | 1b | 1 | 83 | 92 |
| 2[d] | n-Bu | Ph | 1c | 4 | 92 | 99 |
| 3 | 7-Octenyl | Ph | 1d | 14 | 89 | 97 |
| 4 | i-Pr | Ph | 1e | 36 | 83 | 92 |
| 5 | Bn | Ph | 1f | 16 | 88 | 99 |
| 6 | n-Bu | 4-OMe—C$_6$H$_4$ | 1a | 24 | 91 | 99 |
| 7 | i-Pr | 4-OMe—C$_6$H$_4$ | 1g | 36 | 71 | 99 |
| 8 | n-Bu | 4-Cl—C$_6$H$_4$ | 1h | 48 | 76 | 95 |
| 9 | i-Pr | 4-Cl—C$_6$H$_4$ | 1i | 48 | 74 | 88 |
| 10 | n-Bu | 4-F—C$_6$H$_4$ | 1j | 24 | 81 | 91 |
| 11 | n-Bu | 4-Br—C$_6$H$_4$ | 1k | 30 | 86 | 96 |
| 12 | n-Bu | 2-Me—C$_6$H$_4$ | 1l | 24 | 87 | 98 |
| 13 | n-Bu | 3-Me—C$_6$H$_4$ | 1 | 24 | 91 | 99 |
| 14 | n-Bu | 4-Me—C$_6$H$_4$ | 1n | 24 | 94 | 99 |
| 15 | n-Bu | 2-Naph | 1o | 20 | 81 | 97 |

R = alkyl, alkenyl, Bn
R' = aryl
[a] 2 (0.15 mmol; ee > 97% and dr > 20:1), F (0.15 mmol), 1.5 mL toluene, O$_2$ (10 atm).
[b]Isolated yield of 1.
[c]Determined via chiral-phase HPLC.
[d]Reaction at RT.

(2)

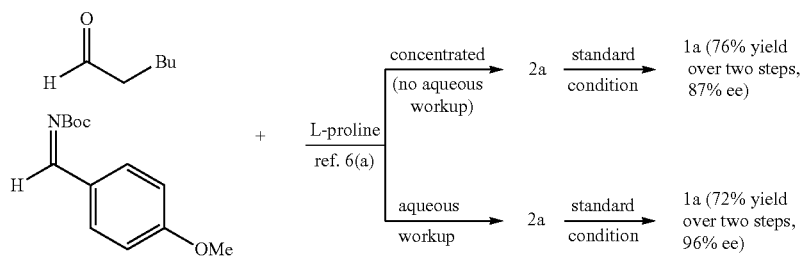

Example 5

(R)-tert-Butyl 2-oxo-1-phenylpropylcarbamate (1b)

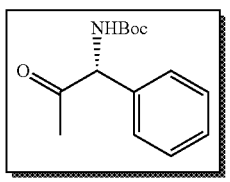

1b

The title compound was prepared according to the general procedure: Yellow oil, 83% yield; HPLC analysis: 92% ee (Chiralcel AD-H, 02:98 $^i$PrOH/Hexane, 0.50 mL/min), R$_t$ (minor)=26.6 min, R$_t$ (major)=39.2 min.

Example 6

(R)-tert-Butyl 2-oxo-1-phenylhexylcarbamate (1c)

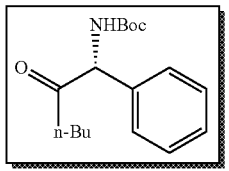

1c

The title compound was prepared according to the general procedure: Yellow oil, 92% yield; HPLC analysis: 99% ee (Chiralcel AD-H, 02:98 $^i$PrOH/Hexane, 0.50 mL/min), R$_t$ (minor)=21.0 min, R$_t$ (major)=31.4 min.

Example 7

(R)-tert-Butyl 2-oxo-1-phenyldec-9-enylcarbamate (1d)

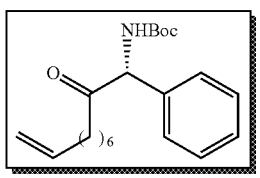

1d

The title compound was prepared according to the general procedure: Yellow oil, 89% yield; $[\alpha]_D^{20}$=−150.3° (c=0.011 g/mL, CHCl$_3$); $^1$H NMR (400 MHz, CDCl$_3$) δ 7.40-7.20 (m, 5H), 5.91 (d, J=5.3 Hz, 1H), 5.74 (m, 1H), 5.26 (d, J=6.3 Hz, 1H), 4.98-4.86 (m, 2H), 2.42-2.26 (m, 2H), 1.96 (dd, J=7.0, 14.3 Hz, 2H), 1.58-1.33 (m, 11H), 1.28-1.20 (m, 3H), 1.21-1.04 (m, 3H); $^{13}$C NMR (100 MHz, CDCl3) δ 206.1, 154.9, 139.0, 137.1, 129.1, 128.4, 127.9, 114.3, 79.8, 64.2, 39.5, 33.6, 28.7, 28.6, 28.3, 23.6; HRMS (ESI) calcd for C$_{23}$H$_{30}$NO$_3$Na (M+Na)+: 368.2226. Found: 368.2238; HPLC analysis: 97% ee (Chiralcel OD-H, 03:97 $^i$PrOH/Hexane, 0.50 mL/min), R$_t$ (major)=14.0 min, R$_t$ (minor)=18.7 min.

Example 8

(R)-tert-Butyl 3-methyl-2-oxo-1-phenylbutylcarbamate (1e)

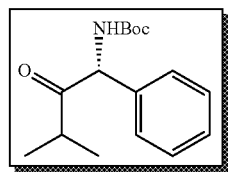

1e

The title compound was prepared according to the general procedure: Yellow oil, 83% yield; $[\alpha]_D^{20}$=−205.5° (c=0.008 g/mL, CHCl$_3$); $^1$H NMR (400 MHz, CDCl$_3$) δ 7.39-7.24 (m, 5H), 5.92 (d, J=4.4 Hz, 1H), 5.42 (d, J=6.5 Hz, 1H), 2.72-2.60 (m, 1H), 1.40 (s, 9H), 1.14 (d, J=7.1 Hz, 3H), 0.84 (d, J=6.6 Hz, 3H); $^{13}$C NMR (100 MHz, CDCl$_3$) δ 209.8, 154.7, 136.9, 129.0, 128.3, 128.0, 79.7, 62.6, 37.5, 28.2, 19.2, 17.9; HRMS (ESI) calcd for C$_{18}$H$_{22}$NO$_3$Na (M+Na)+: 300.1600. Found: 300.1601; HPLC analysis: 92% ee (Chiralcel AD-H, 02:98 $^i$PrOH/Hexane, 0.50 mL/min), R$_t$ (minor)=20.0 min, R$_t$ (major)=27.4 min.

Example 9

(R)-tert-Butyl 2-oxo-1,3-diphenylpropylcarbamate (1f)

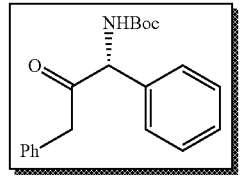

1f

The title compound was prepared according to the general procedure: White solid, 88% yield; $[\alpha]_D^{20}$=−167.5° (c=0.014 g/mL, CHCl$_3$); $^1$H NMR (400 MHz, CDCl$_3$) δ 7.41-7.33 (m, 2H), 7.33-7.19 (m, 6H), 6.98 (dd, J=1.6, 7.6 Hz, 2H), 5.88 (d, J=4.4 Hz, 1H), 5.38 (d, J=6.3 Hz, 1H), 3.65 (bs, 2H), 1.38 (s, 9H); $^{13}$C NMR (100 MHz, CDCl$_3$) δ 203.3, 154.8, 136.6, 133.1, 129.5, 129.2, 128.6, 128.2, 127.2, 79.9, 63.7, 46.3, 28.3; HRMS (ESI) calcd for C$_{20}$H$_{23}$NO$_3$Na (M+Na)+: 348.1576. Found: 348.1587; HPLC analysis: 99% ee (Chiralcel AS-H, 03:97 $^i$PrOH/Hexane, 0.50 mL/min), R$_t$ (minor) =9.6 min, R$_t$ (major)=20.3 min.

Example 10

(R)-tert-Butyl 1-(4-methoxyphenyl)-3-methyl-2-oxobutylcarbamate (1g)

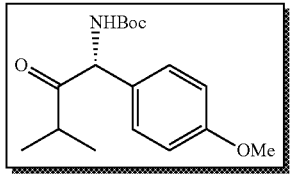

The title compound was prepared according to the general procedure: White solid, 71% yield; $[\alpha]_D^{20}$=−188.0° (c=0.010 g/mL, CHCl$_3$); $^1$H NMR (400 MHz, CDCl$_3$) δ 7.20 (d, J=8.4 Hz, 2H), 6.86 (d, J=8.8 Hz, 2H), 5.86 (d, J=5.5 Hz, 1H), 5.35 (d, J=6.5 Hz, 1H), 3.79 (s, 3H), 2.71-2.58 (m, 1H), 1.40 (s, 9H), 1.12 (d, J=7.1 Hz, 3H), 0.85 (d, J=6.6 Hz, 3H); 13C NMR (100 MHz, CDCl$_3$) δ 210.0, 159.5, 154.8, 129.3, 128.9, 114.4, 79.6, 61.8, 55.2, 37.5, 28.3, 19.2, 18.0; HRMS (ESI) calcd for C$_{17}$H$_{25}$NO$_4$Na (M+Na)+: 330.1681. Found: 330.1685; HPLC analysis: 99% ee (Chiralcel AD-H, 03:97 $^i$PrOH/Hexane, 0.50 mL/min), R$_t$ (minor)=26.0 min, R$_t$ (minor)=33.8 min.

Example 11

(R)-tert-Butyl 1-(4-chlorophenyl)-2-oxohexylcarbamate (1h)

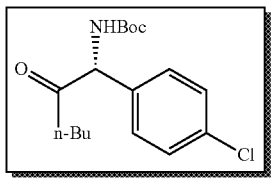

The title compound was prepared according to the general procedure: White solid, 76% yield; $[\alpha]_D^{20}$=−141.1° (c=0.012 g/mL, CHCl$_3$); $^1$H NMR (400 MHz, CDCl$_3$) δ 7.37-7.31 (m, 2H), 7.28-7.20 (m, 2H), 5.96 (d, J=4.8 Hz, 1H), 5.23 (d, J=5.9 Hz, 1H), 2.44-2.25 (m, 2H), 1.56-1.33 (m, 11H), 1.24-1.09 (m, 2H), 0.81 (t, J=7.3 Hz, 3H); $^{13}$C NMR (100 MHz, CDCl$_3$) δ 205.4, 154.7, 135.7, 134.3, 129.2, 129.1, 79.9, 63.4, 39.2, 28.2, 25.6, 22.0, 13.6; HRMS (ESI) calcd for C$_{19}$H$_{23}$NO$_3$Cl (M+1)+: 348.1366. Found: 348.1381; HPLC analysis: 95% ee (Chiralcel AD-H, 02:98 $^i$PrOH/Hexane, 0.50 mL/min), R$_t$ (minor)=22.5 min, R$_t$ (major)=40.8 min.

Example 12

(R)-tert-Butyl 1-(4-chlorophenyl)-3-methyl-2-oxobutylcarbamate (1i)

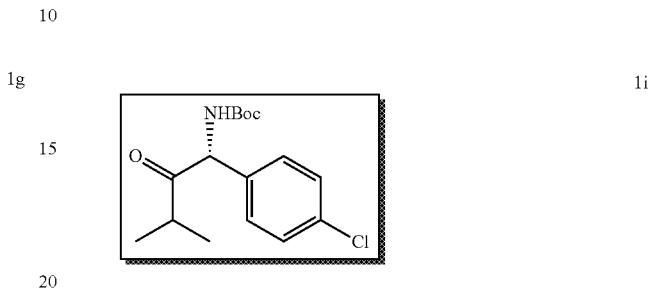

The title compound was prepared according to the general procedure: White solid, 74% yield; $[\alpha]_D^{20}$=−214.0° (c=0.010 g/mL, CHCl$_3$); $^1$H NMR (400 MHz, CDCl$_3$) δ 7.33 (d, J=8.4 Hz, 2H), 7.25 (d, J=8.2 Hz, 2H), 5.98 (d, J=4.8 Hz, 1H), 5.38 (d, J=6.1 Hz, 1H), 2.72-2.58 (m, 1H), 1.40 (s, 9H), 1.14 (d, J=7.0 Hz, 3H), 0.86 (d, J=6.6 Hz, 3H); $^{13}$C NMR (100 MHz, CDCl$_3$) δ 209.2, 154.6, 135.6, 134.3, 129.3, 129.2, 79.9, 61.9, 37.5, 28.2, 19.1, 17.9; HRMS (ESI) calcd for C$_{16}$H$_{23}$NO$_3$Cl (M+1)+: 312.1366. Found: 312.1343; HPLC analysis: 88% ee (Chiralcel AD-H, 02:98 $^i$PrOH/Hexane, 0.50 mL/min), R$_t$ (minor)=20.5 min, R$_t$ (major)=31.8 min.

Example 13

(R)-tert-Butyl 1-(4-fluorophenyl)-2-oxohexylcarbamate (1j)

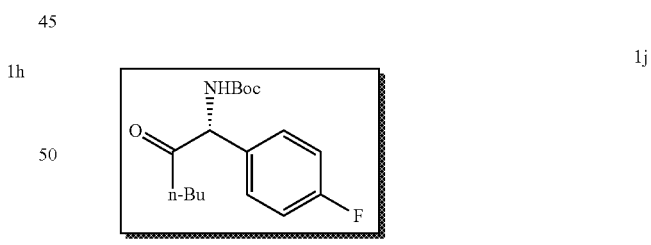

The title compound was prepared according to the general procedure: White solid, 81% yield; $[\alpha]_D^{20}$=−180.5° (c=0.013 g/mL, CHCl$_3$); $^1$H NMR (400 MHz, CDCl$_3$) δ 7.32-7.24 (m, 2H), 7.09-7.02 (m, 2H), 5.94 (d, J=4.7 Hz, 1H), 5.25 (d, J=6.0 Hz, 1H), 2.43-2.27 (m, 2H), 1.57-1.24 (m, 11H), 1.24-1.09 (m, 2H), 0.80 (t, J=7.3 Hz, 3H); $^{13}$C NMR (100 MHz, CDCl$_3$) δ 205.7, 162.6, 154.8, 133.0, 129.6, 129.5, 116.1, 115.9, 79.9, 63.3, 39.2, 28.2, 25.6, 22.0, 13.6; HRMS (ESI) calcd for C$_{17}$H$_{25}$FNO$_3$ (M+1)+: 310.1818. Found: 310.1848; HPLC analysis: 91% ee (Chiralcel AD-H, 03:97 *i*PrOH/Hexane, 0.50 mL/min), $R_t$ (minor)=17.2 min, $R_t$ (major)=30.7 min.

Example 14

(R)-tert-Butyl 1-(4-bromophenyl)-2-oxohexylcarbamate (1k)

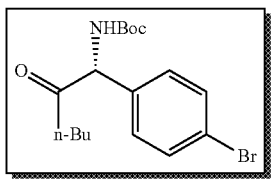

1k

The title compound was prepared according to the general procedure: White solid, 86% yield; $[\alpha]_D^{20}$=−187.0° (c=0.011 g/mL, CHCl$_3$); $^1$H NMR (400 MHz, CDCl$_3$) δ 7.50 (d, J=7.9 Hz, 2H), 7.18 (d, J=7.9 Hz, 2H), 5.96 (d, J=3.2 Hz, 1H), 5.21 (d, J=5.6 Hz, 1H), 2.44-2.26 (m, 2H), 1.58-1.25 (m, 11H), 1.25-1.11 (m, 2H), 0.80 (t, J=7.3 Hz, 3H); $^{13}$C NMR (100 MHz, CDCl$_3$) δ 205.3, 154.7, 136.3, 132.2, 129.4, 122.4, 79.9, 63.5, 39.2, 28.2, 25.6, 22.0, 13.6; HRMS (ESI) calcd for C$_{17}$H$_{24}$NO$_3$BrNa (M+Na)+: 392.0837. Found: 392.0828; HPLC analysis: 96% ee (Chiralcel OD-H, 01:99 *i*PrOH/Hexane, 0.50 mL/min), $R_t$ (major)=14.3 min, $R_t$ (minor)=17.9 min.

Example 15

(R)-tert-Butyl 2-oxo-1-o-tolylhexylcarbamate (1l)

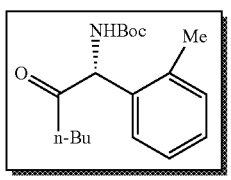

1l

The title compound was prepared according to the general procedure: White solid, 87% yield; $[\alpha]_D^{20}$=−212.3° (c=0.011 g/mL, CHCl$_3$); $^1$H NMR (400 MHz, CDCl$_3$) δ 7.21-7.10 (m, 3H), 7.04 (d, J=7.2 Hz, 1H), 5.76 (d, J=6.4 Hz, 1H), 5.50 (d, J=6.6 Hz, 1H), 2.51 (s, 3H), 2.38-2.17 (m, 2H), 1.56-1.22 (m, 11H), 1.22-1.08 (m, 2H), 0.79 (t, J=7.3 Hz, 3H); 13C NMR (100 MHz, CDCl$_3$) δ 206.4, 154.9, 136.6, 135.2, 131.1, 128.2, 127.5, 126.5, 79.6, 60.7, 39.1, 28.2, 25.6, 21.9, 19.6, 13.5; HRMS (ESI) calcd for C$_{18}$H$_{28}$NO$_3$ (M+1)+: 306.2069. Found: 306.2027; HPLC analysis: 98% ee (Chiralcel OD-H, 02:98 *i*PrOH/Hexane, 0.50 mL/min), $R_t$ (major)=9.6 min, $R_t$ (minor)=13.6 min.

Example 16

(R)-tert-Butyl 2-oxo-1-m-tolylhexylcarbamate (1m)

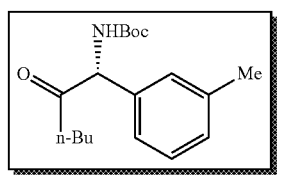

1m

The title compound was prepared according to the general procedure: White solid, 91% yield; $[\alpha]_D^{20}$=−232.0° (c=0.015 g/mL, CHCl$_3$); $^1$H NMR (400 MHz, CDCl$_3$) δ 7.26-7.20 (m, 1H), 7.12-7.01 (m, 2H), 5.87 (d, J=5.5 Hz, 1H), 5.22 (d, J=6.5 Hz, 1H), 2.41-2.26 (m, 5H), 1.56-1.22 (m, 10H), 1.22-1.08 (m, 2H), 0.78 (t, J=7.6 Hz, 3H); $^{13}$C NMR (100 MHz, CDCl$_3$) δ 206.1, 154.8, 138.7, 136.8, 129.1, 128.8, 128.4, 124.8, 79.6, 64.0, 39.1, 28.2, 25.6, 21.9, 21.3, 13.6; HRMS (ESI) calcd for C$_{18}$H$_{28}$NO$_3$ (M+1)+: 306.2069. Found: 306.2027; HPLC analysis: 99% ee (Chiralcel OD-H, 03:97 *i*PrOH/Hexane, 0.50 mL/min), $R_t$ (major)=16.9 min, $R_t$ (minor)=20.3 min.

Example 17

(R)-tert-Butyl 2-oxo-1-p-tolylhexylcarbamate (1n)

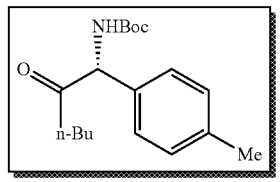

1n

The title compound was prepared according to the general procedure: White solid, 94% yield; $[\alpha]_D^{20}$=−240.3° (c=0.012 g/mL, CHCl$_3$); $^1$H NMR (400 MHz, CDCl$_3$) δ 7.22-7.13 (m, 4H), 5.88 (d, J=5.5 Hz, 1H), 5.24 (d, J=6.4 Hz, 1H), 2.44-2.26 (m, 5H), 1.59-1.26 (m, 11H), 1.25-1.08 (m, 2H), 0.79 (t, J=7.3 Hz, 3H); $^{13}$C NMR (100 MHz, CDCl3) δ 206.1, 154.8, 138.1, 134.0, 129.7, 127.6, 79.6, 63.7, 39.1, 28.2, 25.6, 21.9, 21.0, 13.6; HRMS (ESI) calcd for C$_{18}$H$_{28}$NO$_3$ (M+1)+: 306.2069.

Found: 306.2027; HPLC analysis: 99% ee (Chiralcel AD-H, 02:98 $^i$PrOH/Hexane, 0.50 mL/min), $R_t$ (minor)=23.8 min, $R_t$ (major)=32.0 min.

Example 18

(R)-tert-Butyl 1-(naphthalen-2-yl)-2-oxohexylcarbamate (1o)

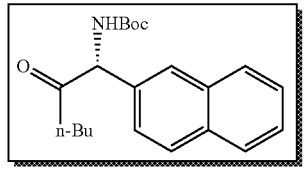

1o

The title compound was prepared according to the general procedure: White solid, 81% yield; $[\alpha]_D^{20}$=−227.5° (c=0.010 g/mL, CHCl$_3$); $^1$H NMR (400 MHz, CDCl$_3$) δ 7.86-7.78 (m, 4H), 7.55-7.43 (m, 2H), 7.38-7.31 (m, 1H), 6.05 (d, J=5.4 Hz, 1H), 5.44 (d, J=6.2 Hz, 1H), 2.49-2.28 (m, 2H), 1.60-1.32 (m, 11H), 1.21-1.06 (m, 2H), 0.77 (t, J=7.3 Hz, 3H); $^{13}$C NMR (100 MHz, CDCl$_3$) δ 206.0, 154.8, 134.5, 133.3, 133.1, 129.0, 128.0, 127.7, 127.5, 126.4, 124.9, 79.8, 64.2, 39.4, 28.2, 25.6, 22.0, 13.6; HRMS (ESI) calcd for C$_{21}$H$_{28}$NO$_3$ (M+1)+: 342.2069. Found: 342.2091; HPLC analysis: 97% ee (Chiralcel OD-H, 01:99 $^i$PrOH/Hexane, 0.50 mL/min), $R_t$ (major)=19.2 min, $R_t$ (minor)=22.3 min.

Example 19

Synthesis of α,α'-Diamino Ketones

The oxidative cleavage approach was extended to the asymmetric synthesis of α,α'-diaminoketones (Table 3). The precursor aldehyde 4a was first subjected to the standard condition used in Table 2 (1 equiv F, 10 atm O$_2$). However, the ketone product 3a was obtained as a diastereomeric mixture (dr~7:3). Additional studies showed that the residual amine F could mediate the epimerization of the ketone product. By lowering the amine F to 0.7 equivalent, product 3a could be obtained with acceptable yield and essentially as a single diastereomer with 97% ee. The α,α'-diaminoketone products can be easily transferred to optically pure diamino alcohols (eq 3), analogues of such amino alcohols are key fragments in HIV-1 protease inhibitors.

To a Parr's high pressure reactor equipped with a magnetic stir bar were added diamino aldehyde 4a (0.050 g, 0.11 mmol), p-methoxy aniline (0.009 g, 0.07 mmol) and toluene (1.5 mL). The reactor was then filled with O$_2$ to a reach a pressure of 10 atmospheres. The reaction mixture was stirred at room temperature for 1 h followed by 36 hours at 50° C. After complete consumption of the amine (via the corresponding imine/enamine intermediate), as indicated by TLC (and crude $^1$H NMR analysis when necessary), the reaction mixture was concentrated in vacuo. Column chromatography (hexanes: EtOAc) of the resulting residue gave the desired α,α'-diamino ketone 3a (0.030 g, 0.06 mmol) as a white solid in 62% yield.

TABLE 3

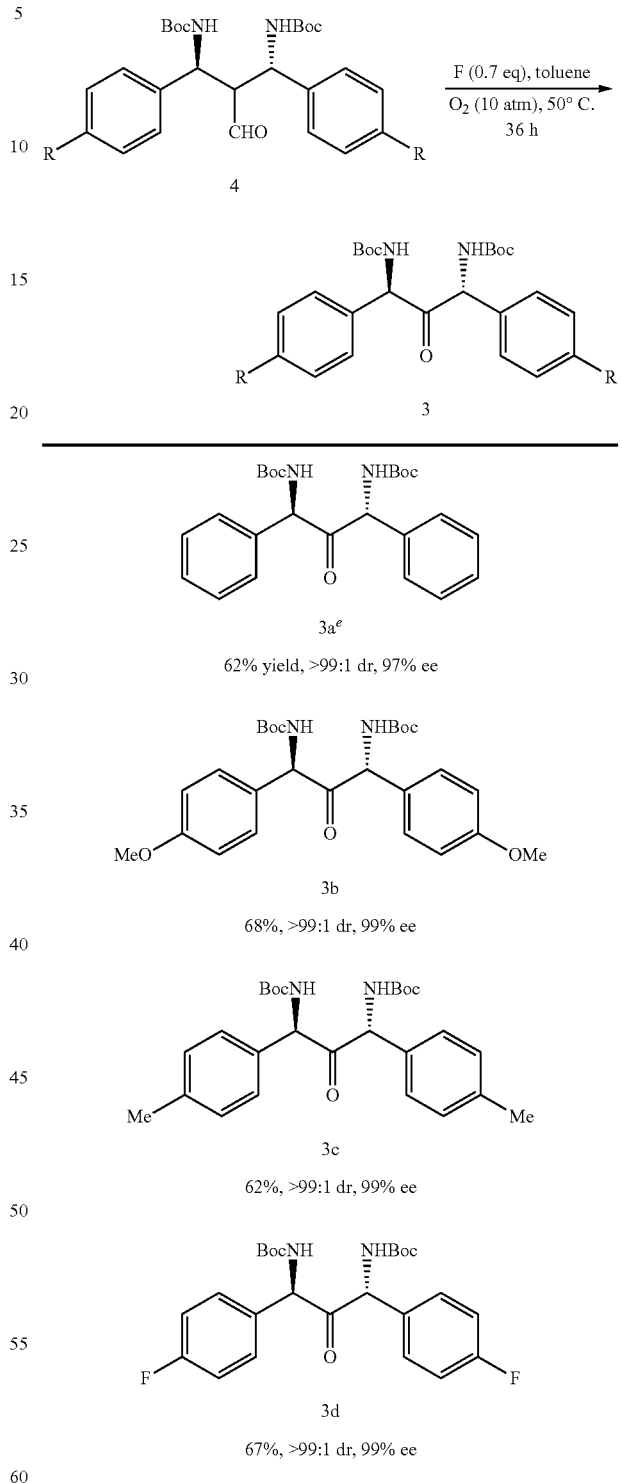

Synthesis of α,α'-diaminoketones.[a,b,c,d]

[a]4 (0.10 mmol; ee > 99%; dr > 20:1), F (0.07 mmol), O$_2$ (10 atm), 1.5 mL toluene.
[b]Isolated yield.
[c]dr was determined via $^1$H NMR.
[d]ee was determined via chiral-phase HPLC.
$^e$Reaction time was 16 h.

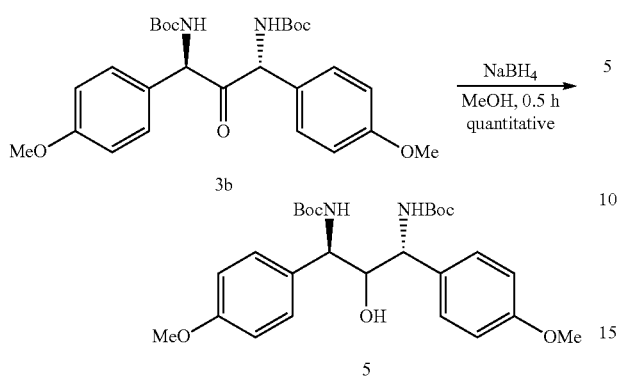

Example 20 tert-Butyl (1R,3R)-2-oxo-1,3-diphenylpropane-1,3-diyldicarbamate (3a)

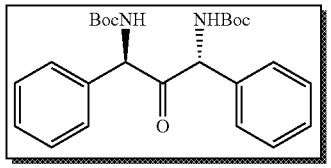

The title compound was prepared according to the general procedure: White solid, 62% yield; $[\alpha]_D^{20}=-195.5°$ (c 1.5, CHCl$_3$); $^1$H NMR (400 MHz, CDCl$_3$) δ 7.43-7.30 (m, 5H), 7.26-7.14 (m, 5H), 5.78 (bs, 2H), 5.23 (d, J=6.3 Hz, 2H), 1.33 (s, 18H); $^{13}$C NMR (100 MHz, CDCl$_3$) δ 201.7, 154.3, 136.2, 129.4, 128.8, 128.1, 79.9, 60.6, 28.1; HRMS (ESI) calcd for C$_{25}$H$_{32}$N$_2$O$_5$Na (M+Na)+: 463.2209. Found: 463.2218; HPLC analysis: 97% ee (Chiralcel OD-H, 02:98 $^i$PrOH/Hexane, 0.50 mL/min), R$_t$ (major)=22.7 min, R$_t$ (minor)=25.1 min.

Example 21 tert-Butyl (1R,3R)-1,3-bis(4-methoxyphenyl)-2-oxopropane-1,3-giyldicarbamate (3b)

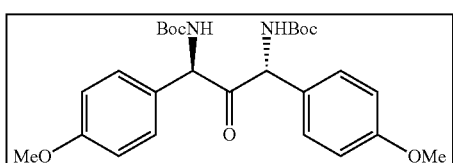

The title compound was prepared according to the general procedure: White solid, 68% yield; $[\alpha]_D^{20}=-177.3°$ (c=0.013 g/mL, CHCl$_3$); $^1$H NMR (400 MHz, CDCl$_3$) δ 7.12 (d, J=7.7 Hz, 4H), 6.90 (d, J=8.5 Hz, 4H), 5.73 (bs, 2H), 5.18 (d, J=6.2 Hz, 2H), 3.82 (s, 6H), 1.34 (s, 18H); $^{13}$C NMR (100 MHz, CDCl$_3$) δ 202.1, 159.9, 154.4, 129.3, 128.3, 114.8, 79.8, 60.2, 55.3, 28.2; HRMS (ESI) calcd for C$_{27}$H$_{36}$N$_2$O$_7$Na (M+Na)+: 523.2420. Found: 523.2437; HPLC analysis: 99% ee (Chiralcel OD-H, 02:98 $^i$PrOH/Hexane, 0.50 mL/min), R$_t$ (minor)=37.3 min, R$_t$ (major)=41.3 min.

Example 22 tert-Butyl (1R,3R)-2-oxo-1,3-dip-tolylpropane-1,3-diyldicarbamate (3c)

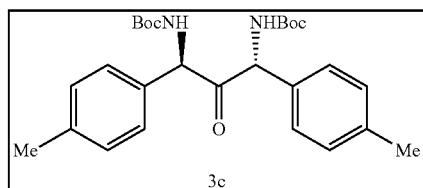

The title compound was prepared according to the general procedure: White solid, 62% yield; $[\alpha]_D^{20}=-179.2°$ (c=0.011 g/mL, CHCl$_3$); $^1$H NMR (400 MHz, CDCl$_3$) δ 7.17 (d, J=7.7 Hz, 4H), 7.08 (d, J=6.9 Hz, 4H), 5.75 (bs, 2H), 5.18 (d, J=6.4 Hz, 2H), 2.35 (s, 6H), 1.33 (s, 18H); $^{13}$C NMR (100 MHz, CDCl$_3$) δ 202.0, 154.4, 138.7, 133.3, 130.1, 128.0, 79.8, 60.7, 28.3, 21.2; HRMS (ESI) calcd for C$_{27}$H$_{36}$N$_2$O$_5$Na (M+Na)+: 491.2522. Found: 491.2506; HPLC analysis: 99% ee (Chiralcel OD-H, 02:98 $^i$PrOH/Hexane, 0.50 mL/min), R$_t$ (major)=15.8 min, R$_t$ (minor)=18.8 min.

Example 23 tert-Butyl (1R,3R)-1,3-bis(4-fluorophenyl)-2-oxopropane-1,3-diyldicarbamate (3d)

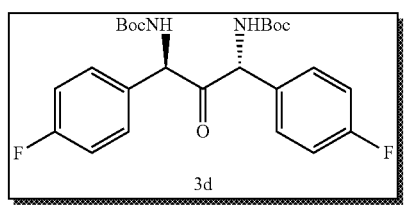

The title compound was prepared according to the general procedure: White solid, 68% yield; $[\alpha]_D^{20}=-189.3°$ (c=0.008 g/mL, CHCl$_3$); $^1$H NMR (400 MHz, CDCl$_3$) δ 7.27-7.16 (m, 4H), 7.15-7.06 (m, 4H), 5.72 (bs, 2H), 5.20 (d, J=5.9 Hz, 2H), 1.35 (s, 18H); $^{13}$C NMR (100 MHz, CDCl$_3$) δ 201.5, 162.9, 154.3, 131.8, 129.6, 129.8, 116.6, 116.3, 80.2, 60.2, 28.2; HRMS (ESI) calcd for C$_{25}$H$_{30}$N$_2$O$_5$Na (M+Na)+: 499.2020.

Found: 499.2018; HPLC analysis: 99% ee (Chiralcel OD-H, 02:98 'PrOH/Hexane, 0.50 mL/min), $R_t$ (minor)=19.8 min, $R_t$ (major)=37.3 min.

Example 24

Synthesis of Diamino Ketones to Diamino Alcohols (Key-Subunit of HIV-1Protease Inhibitor): tert-Butyl (1R,3R)-2-hydroxy-1,3-bis(4-methoxyphenyl)propane-1,3-diyldicarbamate (5)

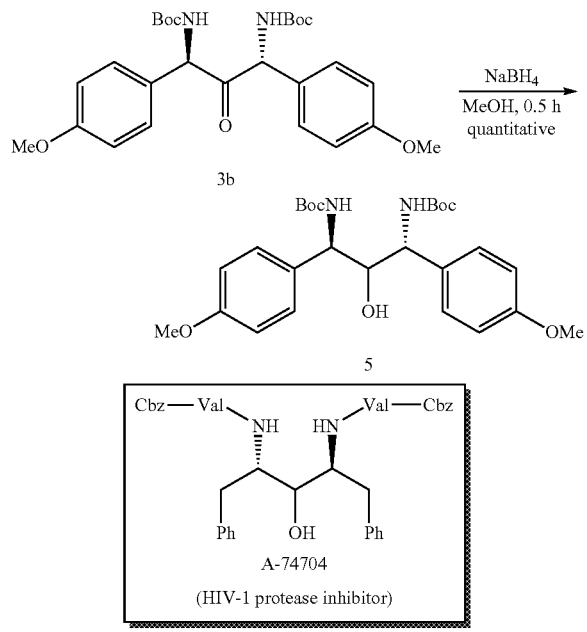

Clear oil, quantitative yield; $[\alpha]_D^{20}$=−151.3° (c=0.011 g/mL, CHCl$_3$); $^1$H NMR (400 MHz, CDCl$_3$) δ 7.17 (d, J=8.4 Hz, 2H), 7.10 (d, J=8.6 Hz, 2H), 6.86 (t, J=8.2 Hz, 4H), 5.51 (bs, 1H), 5.00 (d, J=6.2 Hz, 1H), 4.45 (bs, 1H), 4.32 (t, J=7.1 Hz, 1H), 4.21 (bs, 1H), 3.79 (s, 6H), 3.62 (bs, 1H); $^{13}$C NMR (100 MHz, CDCl$_3$) δ 159.3, 159.0, 155.2, 130.2, 129.3, 128.5, 114.2, 113.8, 80.1, 79.5, 56.2, 55.2, 55.1, 28.3, 28.2; HRMS (ESI) calcd for $C_{27}H_{39}N_2O_7$(M+1)+: 503.2757. Found: 503.2742.

Example 25

Synthesis of β-Nitro Ketones

The applicability of present methods in preparing chiral α-functionalized ketones was further demonstrated. β-nitro ketones 6 were synthesized via C—C bond cleavage of the corresponding readily available γ-nitro aldehydes (Table 4). The use of metal-based oxidants or catalysts was again not successful. The metal-free conditions under molecular O$_2$ used above worked effectively here after a very slight modification (e.g., using 0.9 equivalent of amine F, to avoid ketone product racemization). The scope of the reaction was briefly examined (Table 4). Aldehydes (7) with R as both n-alkyl and branched alkyl substituents could give the products with good ees and yields (Table 4, 6b & 6c). The R' substituents could be either aryls or alkyls, except that when electron-deficient aryl substituent (Table 4, 6e) was present, the initial β-nitro ketone product (stable during the C—C cleaving reaction and crude $^1$H-NMR analysis) underwent subsequent E$_2$-elimination during SiO$_2$ column chromatography. It's worth to note that aldehyde substrates (7) with relatively low dr could be used to give high ee ketone products (6).

To a Parr's high pressure reactor equipped with a magnetic stir bar were added aldehyde 7a (0.05 g, 0.24 mmol), p-methoxy aniline (0.026 g, 0.21 mmol) and toluene (1.5 mL). The reactor was then filled with O$_2$ to a reach a pressure of 10 atmospheres. The reaction mixture was stirred at room temperature for 1 h followed by 48 hour at 50° C. After the aldehyde was nearly completely consumed (when no imine/enamine was detected), as indicated by TLC (and crude $^1$H NMR analysis when necessary), the reaction mixture was concentrated in vacuo. Column chromatography (hexanes: EtOAc) of the resulting residue gave the desired β-nitro ketone 6a (0.035 g, 0.18 mmol) as a yellowish oil in 76% yield.

TABLE 4

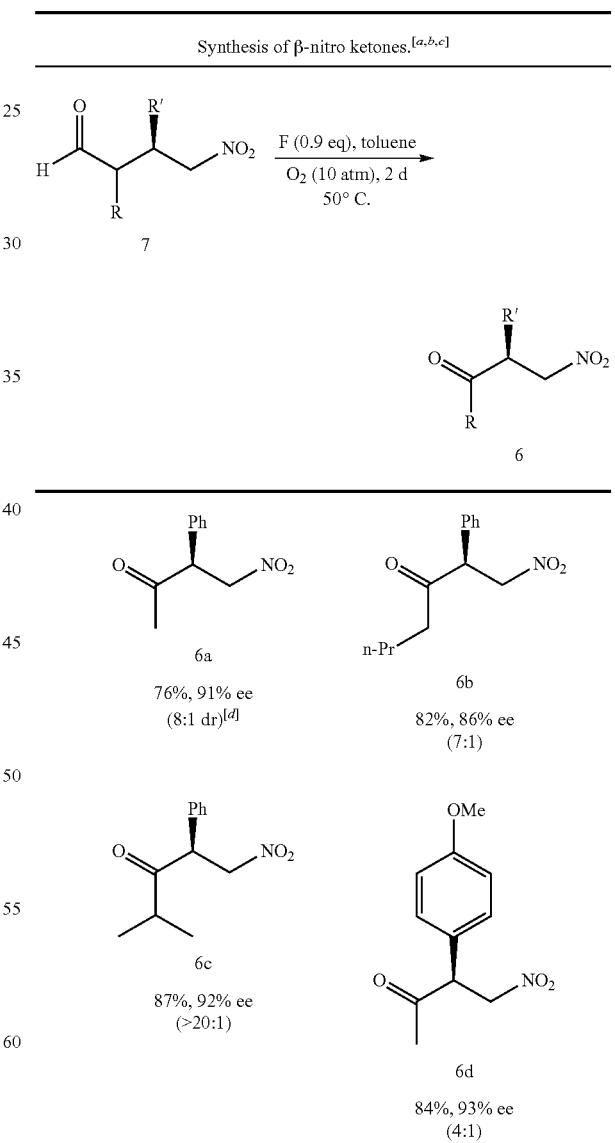

TABLE 4-continued

Synthesis of β-nitro ketones.[a,b,c]

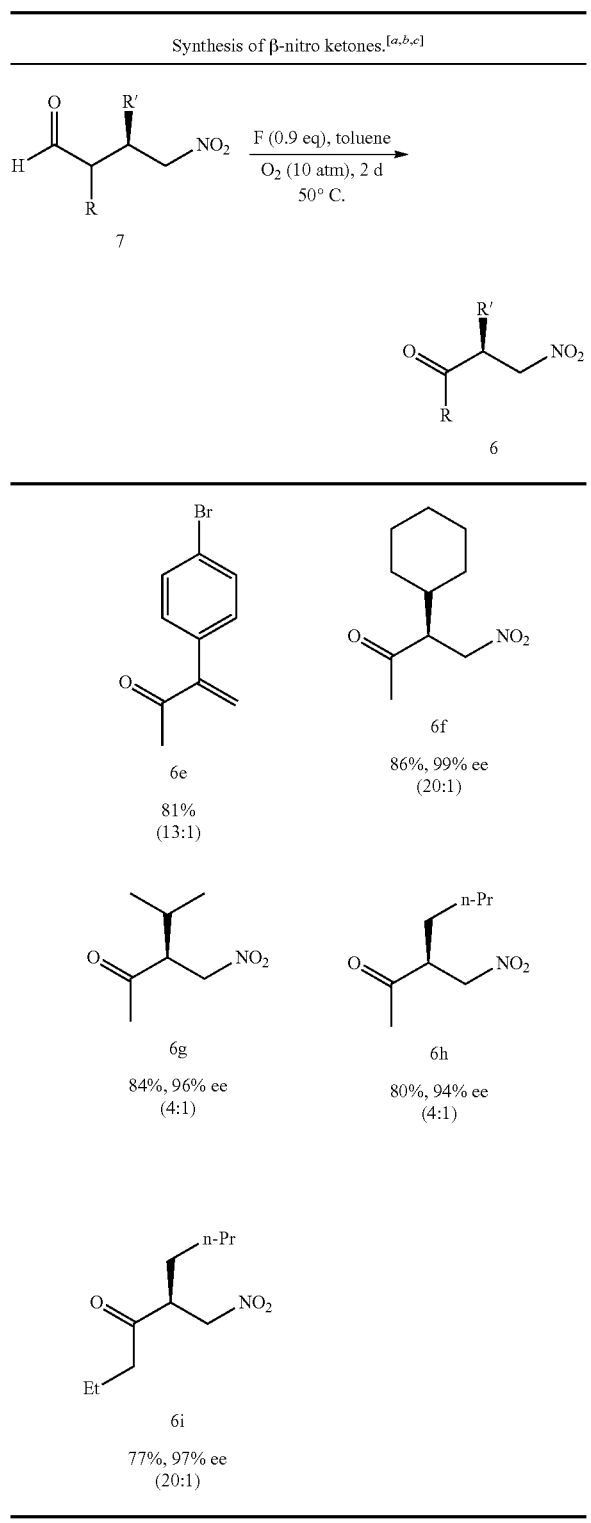

R = alkyl
R' = alkyl, cycloalkyl, aryl

[a]7 (0.24 mmol), F (0.21 mmol), O$_2$ (10 atm), toluene (1.5 mL).
[b]Isolated yield.
[c]ee was determined via chiral-phase HPLC.
[d]dr of the aldehyde substrates (7).

Example 26

(S)-4-Nitro-3-phenylbutan-2-one (6a)

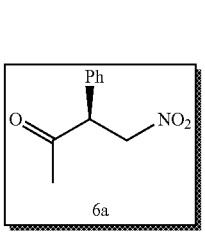

The title compound was prepared according to the general procedure: Yellow oil, 76% yield; $[\alpha]_D^{20}$=−254.6° (c=0.010 g/mL, CHCl$_3$); $^1$H NMR (400 MHz, CDCl$_3$) δ 7.42-7.33 (m, 3H), 7.23-7.18 (m, 2H), 5.14 (dd, J=9.2, 14.5 Hz, 1H), 4.54 (dd, J=5.3, 9.1 Hz, 1H), 4.45 (dd, J=5.3, 14.5 Hz, 1H), 2.17 (s, 3H); $^{13}$C NMR (100 MHz, CDCl$_3$) δ 204.1, 132.8, 129.7, 128.9, 128.3, 75.2, 55.8, 28.7, HRMS (ESI) calcd for C10H12NO3 (M+1)+: 194.0817, Found: 194.0802; HPLC analysis: 91% ee (Chiralcel AS-H, 02:98 $^i$PrOH/Hexane, 0.50 mL/min), R$_t$ (minor)=57.7 min, R$_t$ (major)=65.3 min.

Example 27

(S)-1-Nitro-2-phenylheptan-3-one (6b)

The title compound was prepared according to the general procedure: Yellow oil, 82% yield; $[\alpha]_D^{20}$=−191.5° (c=0.012 g/mL, CHCl$_3$); $^1$H NMR (400 MHz, CDCl$_3$) δ 7.40-7.30 (m, 3H), 7.19 (dd, J=1.6, 7.6 Hz, 2H), 5.14 (dd, J=9.1, 14.4 Hz, 1H), 4.52 (dd, J=5.2, 9.3 Hz, 1H), 4.44 (dd, J=5.1, 14.4 Hz, 1H), 2.54-2.35 (m, 2H), 1.60-1.41 (m, 2H), 1.27-1.11 (m, 2H), 0.81 (t, J=7.3 Hz, 3H); $^{13}$C NMR (100 MHz, CDCl3) δ 206.5, 132.9, 129.5, 128.7, 128.3, 75.2, 55.1, 41.0, 25.5, 21.9, 13.6; HRMS (ESI) calcd for C$_{13}$H$_{17}$NO$_3$Na (M+Na)+: 258.1106. Found: 258.1125; HPLC analysis: 86% ee (Chiralcel AS-H, 03:97 $^i$PrOH/Hexane, 0.50 mL/min), R$_t$ (major)=31.1 min, R$_t$ (minor)=34.4 min.

Example 28

(S)-4-Methyl-1-nitro-2-phenylpentan-3-one (6c)

The title compound was prepared according to the general procedure: Yellow oil, 87% yield; $[\alpha]_D^{20}$=−169.5 (c=0.011 g/mL, CHCl$_3$); $^1$H NMR (400 MHz, CDCl$_3$) δ 7.42-7.32 (m, 3H), 7.23-7.18 (m, 2H), 5.15 (dd, J=9.6, 14.6 Hz, 1H), 4.71 (dd, J=9.6, 5.0 Hz, 1H), 4.44 (dd, J=5.0, 14.6 Hz, 1H), 2.78-2.66 (m, 1H), 1.18 (d, J=7.1 Hz, 3H), 0.93 (d, J=6.7 Hz, 3H); $^{13}$C NMR (100 MHz, CDCl3) δ 210.1, 132.9, 129.5, 128.7, 128.4, 75.3, 53.5, 39.4, 18.9, 17.9; HRMS (ESI) calcd for C$_{12}$H$_{16}$NO$_3$ (M+1)+: 222.1130. Found: 222.1114; HPLC analysis: 92% ee (Chiralcel AS-H, 05:95 $^i$PrOH/Hexane, 0.50 mL/min), R$_t$ (major)=21.0 min, R$_t$ (minor)=27.1 min.

Example 29

(S)-3-(4-Methoxyphenyl)-4-nitrobutan-2-one (6d)

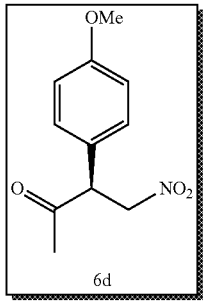

The title compound was prepared according to the general procedure: Yellow oil, 84% yield; $[\alpha]_D^{20}$=−320.5° (c=0.010 g/mL, CHCl$_3$); $^1$H NMR (400 MHz, CDCl$_3$) δ 7.12 (d, J=8.8 Hz, 2H), 6.90 (d, J=8.8 Hz, 2H), 5.08 (dd, J=8.6, 14.0 Hz, 1H), 4.49-4.37 (m, 2H), 3.80 (s, 3H), 2.16 (s, 3H); $^{13}$C NMR (100 MHz, CDCl3) δ 204.3, 159.8, 129.4, 124.5, 115.0, 75.2, 55.2, 55.0, 28.5; HRMS (ESI) calcd for C$_{11}$H$_{14}$NO$_4$ (M+1)+: 224.0923. Found: 224.0936; HPLC analysis: 93% ee (Chiralcel AS-H, 10:90 $^i$PrOH/Hexane, 0.50 mL/min), R$_t$ (minor)=52.5 min, R$_t$ (major)=60.2 min.

Example 30

3-(4-Bromophenyl)but-3-en-2-one (6e)

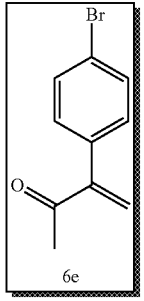

The title compound was prepared according to the general procedure: Yellow oil, 81% yield; $^1$H NMR (400 MHz, CDCl$_3$) δ 7.52-7.47 (m, 2H), 7.21-7.17 (m, 2H), 6.21 (s, 1H), 6.01 (s, 1H), 2.45 (s, 3H); $^{13}$C NMR (100 MHz, CDCl$_3$) δ 198.7, 148.3, 135.7, 131.2, 130.2, 126.6, 122.4, 27.4; HRMS (ESI) calcd for C$_{10}$H$_{10}$OBr (M+1)+: 224.9915. Found: 224.9901.

Example 31

(S)-3-Cyclohexyl-4-nitrobutan-2-one (6f)

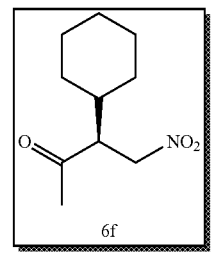

The title compound was prepared according to the general procedure: Yellow oil, 86% yield; $[\alpha]_D^{20}$=−82.5° (c=0.016 g/mL, CHCl$_3$); $^1$H NMR (400 MHz, CDCl$_3$) δ 4.85 (dd, J=10.7, 14.8 Hz, 1H), 4.35 (dd, J=3.3, 14.8 Hz, 1H), 3.34-3.28 (m, 1H), 2.30 (s, 3H), 1.86-1.58 (m, 6H), 1.35-1.09 (m, 4H), 1.01-0.87 (m, 1H); $^{13}$C NMR (100 MHz, CDCl$_3$) δ 207.7, 73.2, 54.5, 38.2, 31.1, 30.6, 29.5, 26.3, 26.2, 25.8; HRMS (ESI) calcd for C$_{10}$H$_{18}$NO$_3$ (M+1)+: 200.1287. Found: 200.1286; HPLC analysis: 99% ee (Chiralcel AS-H, 05:95 $^i$PrOH/Hexane, 0.50 mL/min), R$_t$ (major)=27.3 min, R$_t$ (minor)=37.4 min.

Example 32

(S)-4-Methyl-3-(nitromethyl)pentan-2-one (6g)

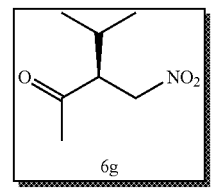

The title compound was prepared according to the general procedure: Yellow oil, 84% yield; $[\alpha]_D^{20}$=−36.5° (c=0.005 g/mL, CHCl$_3$); $^1$H NMR (400 MHz, CDCl$_3$) δ 4.85 (dd, J=10.6, 14.7 Hz, 1H), 4.33 (dd, J=3.3, 14.8 Hz, 1H), 3.31-3.23 (m, 1H), 2.30 (s, 3H), 2.14-2.02 (m, 1H), 1.05 (d, J=6.9 Hz, 3H), 0.90 (d, J=6.9 Hz, 3H); $^{13}$C NMR (100 MHz, CDCl$_3$) 207.6, 72.8, 54.8, 30.4, 28.2, 20.7, 18.8; HRMS (ESI) calcd for C$_7$H$_{14}$NO$_3$ (M+1)+: 160.0974. Found: 160.0973;

HPLC analysis: 96% ee (Chiralcel AS-H, 05:95 $^i$PrOH/Hexane, 0.50 mL/min), $R_t$ (major)=19.8 min, $R_t$ (minor)=25.7 min.

Example 33

(S)-3-(Nitromethyl)heptan-2-one (6h)

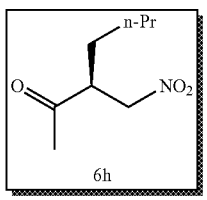

The title compound was prepared according to the general procedure: Yellow oil, 80% yield; $[\alpha]_D^{20}$=−54.0° (c=0.015 g/mL, CHCl$_3$); $^1$H NMR (400 MHz, CDCl$_3$) δ 4.80 (dd, J=9.7, 14.6 Hz, 1H), 4.34 (dd, J=14.6, 4.2 Hz, 1H), 3.40-3.32 (m, 1H), 2.29 (s, 3H), 1.71-1.60 (m, 1H), 1.48 (dt, J=21.4, 7.2 Hz, 1H), 1.40-1.23 (m, 4H), 0.90 (t, J=7.1 Hz, 3H); $^{13}$C NMR (100 MHz, CDCl$_3$) δ 207.6, 74.4, 48.9, 29.2, 28.5, 28.3, 22.4, 13.5; HRMS (ESI) calcd for C$_8$H$_{16}$NO$_3$ (M+1)+: 174.1130. Found: 174.1135; HPLC analysis: 94% ee (Chiralcel AS-H, 05:95 $^i$PrOH/Hexane, 0.50 mL/min), $R_t$ (major)=25.9 min, $R_t$ (minor)=38.1 min.

Example 34

(S)-5-(Nitromethyl)nonan-4-one (6i)

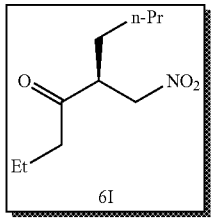

The title compound was prepared according to the general procedure: Yellow oil, 77% yield; $[\alpha]_D^{20}$=−55.2° (c=0.014 g/mL, CHCl$_3$); $^1$H NMR (400 MHz, CDCl$_3$) δ 4.81 (dd, J=9.8, 14.6 Hz, 1H), 4.33 (dd, J=4.2, 14.5 Hz, 1H), 3.38-3.26 (m, 1H), 2.63-2.48 (m, 2H), 1.72-1.51 (m, 3H), 1.50-1.39 (m, 1H), 1.38-1.21 (m, 4H), 0.97-0.83 (m, 6H); $^{13}$C NMR (100 MHz, CDCl$_3$) δ 209.8, 74.6, 48.4, 44.1, 28.7, 28.6, 22.5, 16.7, 13.6; HRMS (ESI) calcd for C$_{10}$H$_{20}$NO$_3$ (M+1)+: 202.1443. Found: 202.1438; HPLC analysis: 97% ee (Chiralcel AS-H, 05:95 $^i$PrOH/Hexane, 0.50 mL/min), $R_t$ (major)=16.7 min, $R_t$ (minor)=18.4 min.

By "comprising" it is meant including, but not limited to, whatever follows the word "comprising". Thus, use of the term "comprising" indicates that the listed elements are required or mandatory, but that other elements are optional and may or may not be present.

By "consisting of" is meant including, and limited to, whatever follows the phrase "consisting of". Thus, the phrase "consisting of" indicates that the listed elements are required or mandatory, and that no other elements may be present.

The inventions illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

By "about" in relation to a given numerical value, such as for temperature and period of time, it is meant to include numerical values within 10% of the specified value.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

The invention claimed is:

1. A method of preparing a chiral α- or β-substituted ketone from the corresponding β- or γ-substituted aldehyde, wherein the ketone has formula (I), (III) or (V),

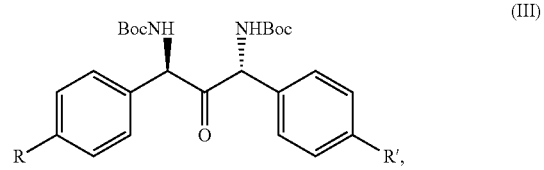

and the corresponding aldehyde has formula (II), (IV) or (VI), respectively,

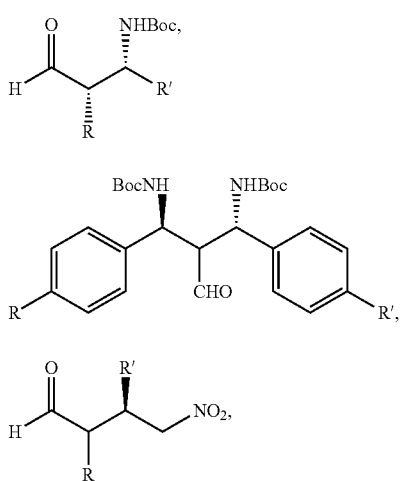

(II)

(IV)

(VI)

the method comprising reacting the aldehyde in the presence of an amine, oxygen and an organic solvent, wherein the reaction is carried out in the absence of a metal-based catalyst or a metal-based oxidant, wherein:

R is H, a substituted or unsubstituted $C_1$-$C_{10}$ alkyl, substituted or unsubstituted $C_2$-$C_{15}$ alkenyl, substituted or unsubstituted $C_2$-$C_{15}$ alkynyl, substituted or unsubstituted $C_3$-$C_{15}$ cycloalkyl, substituted or unsubstituted $C_3$-$C_{15}$ cycloalkenyl, substituted or unsubstituted $C_3$-$C_{15}$ heterocycloalkyl, substituted or unsubstituted $C_3$-$C_{15}$ heterocycloalkenyl, substituted or unsubstituted $C_6$-$C_{15}$ aryl, or substituted or unsubstituted $C_6$-$C_{15}$ heteroaryl; and R' is H, a substituted or unsubstituted $C_1$-$C_{10}$ alkyl, substituted or unsubstituted $C_2$-$C_{15}$ alkenyl, substituted or unsubstituted $C_2$-$C_{15}$ alkynyl, substituted or unsubstituted $C_3$-$C_{15}$ cycloalkyl, substituted or unsubstituted $C_3$-$C_{15}$ cycloalkenyl, substituted or unsubstituted $C_3$-$C_{15}$ heterocycloalkyl, substituted or unsubstituted $C_3$-$C_{15}$ heterocycloalkenyl, substituted or unsubstituted $C_6$-$C_{15}$ aryl, or substituted or unsubstituted $C_6$-$C_{15}$ heteroaryl.

2. The method of claim 1, wherein the amine is a compound of formula (VII),

 (VII), wherein:

$R_1$ is a substituted or unsubstituted alkylaryl, substituted or unsubstituted aryl, substituted or unsubstituted heteroaryl, substituted or unsubstituted alicyclic, substituted or unsubstituted heteroalicyclic, substituted or unsubstituted alkylcycloalkyl, or substituted or unsubstituted alkylheterocycloalkyl; and $R_2$ is H or combines with $R_1$ to form with the nitrogen to which they are attached a cyclic group selected from substituted or unsubstituted heterocycloalkyl and substituted or unsubstituted heteroaryl.

3. The method of claim 2, wherein the amine of formula (VII) is selected from the group consisting of

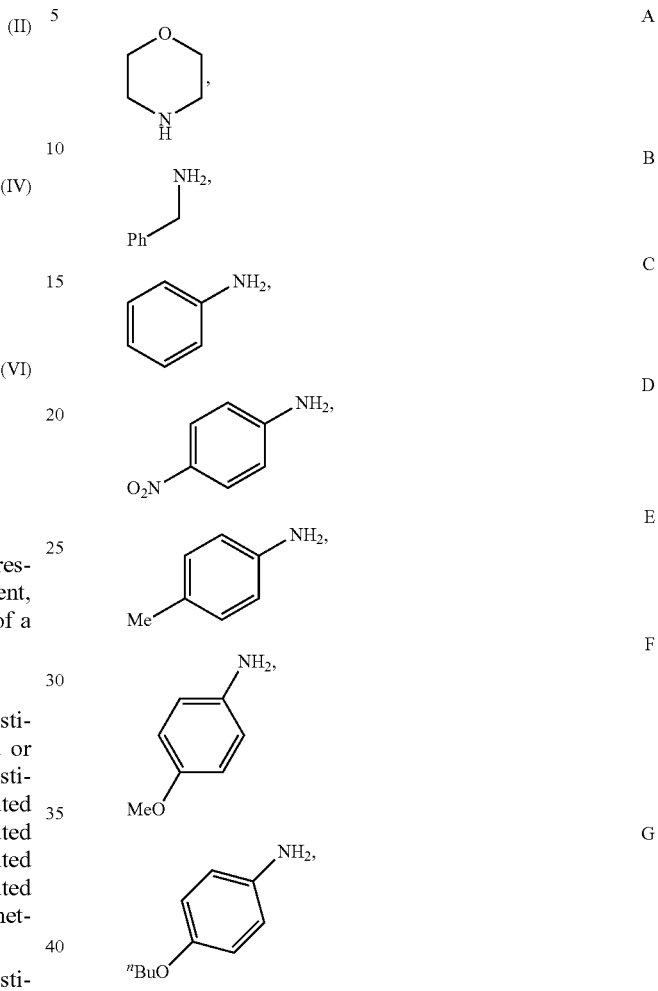

and mixtures thereof.

4. The method of claim 3, wherein the amine of formula (VII) is

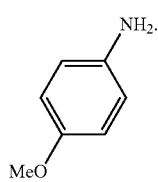

F

5. The method of claim 1, wherein the organic solvent is toluene, $CH_2CN$ or $CH_3Cl$.

6. The method of claim 5, wherein the organic solvent is toluene.

7. The method of claim 1, wherein reacting comprises heating the aldehyde of formula (II), (IV) or (VI) at a temperature range of between 40 and 80° C.

8. The method of claim 7, wherein reacting comprises heating the aldehyde of formula (II), (IV) or (VI) at 50° C.

9. The method of claim 7, wherein heating of the aldehyde of formula (II), (IV) or (VI) is carried out for a period of between 1 and 48 h.

10. The method of claim 9, wherein heating of the aldehyde of formula (II), (IV) or (VI) is carried out for a period of between 4 and 24 h.

11. The method of claim 1, wherein the reaction is carried out at a pressure of between 1 and 15 atm.

12. The method of claim 11, wherein the reaction is carried out at 10 atm.

13. The method of claim 1, wherein the ketone has formula (I) and the corresponding aldehyde has formula (III), wherein R is selected from the group consisting of methyl, i-propyl, n-butyl, benzyl and 7-octenyl.

14. The method of claim 1, wherein the ketone has formula (I) and the corresponding aldehyde has formula (II), wherein R' is selected from the group consisting of phenyl, 4-OMe-$C_6H_4$, 4-Cl—$C_6H_4$, 4-F—$C_6H_4$, 4-Br—$C_6H_4$, 2-Me-$C_6H_4$, 3-Me-$C_6H_4$, 4-Me-$C_6H_4$, and 2-Naph.

15. The method of claim 1, wherein the ketone has formula (III) and the corresponding aldehyde has formula (IV), wherein each of R and R' is independently selected from the group consisting of H, F, methyl and methoxy.

16. The method of claim 1, wherein the ketone has formula (V) and the corresponding aldehyde has formula (VI), wherein R is selected from the group consisting of methyl, i-propyl, n-propyl, and n-butyl.

17. The method of claim 1, wherein the ketone has formula (V) and the corresponding aldehyde has formula (VI), wherein R' is selected from the group consisting of phenyl, 4-OMe-$C_6H_4$, 4-Cl—$C_6H_4$, 4-F—$C_6H_4$, 4-Br—$C_6H_4$, $C_6H_{11}$, i-propyl, and n-butyl.

18. The method of claim 1, wherein the oxygen is provided by carrying out the reaction in the presence of an oxygen-containing atmosphere, such as air.

* * * * *